(12) United States Patent
Burnett et al.

(10) Patent No.: US 6,300,505 B1
(45) Date of Patent: Oct. 9, 2001

(54) METHOD AND APPARATUS FOR IMPROVING THE UNIFORMITY OF DISTRIBUTION OF A PHOSPHORUS-CONTAINING AGENT THROUGHOUT A MALEIC ANHYDRIDE CATALYTIC REACTOR

(75) Inventors: Joseph C. Burnett, Austin, TX (US); William H. Alumbaugh, Pensacola; Lamar A. Reeves, Cantonment, both of FL (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 09/566,421

(22) Filed: May 8, 2000

Related U.S. Application Data

(60) Provisional application No. 60/134,923, filed on May 19, 1999.

(51) Int. Cl.[7] ................................................. C07D 307/60
(52) U.S. Cl. ............................................................ 549/259
(58) Field of Search ............................................. 549/259

(56) References Cited

U.S. PATENT DOCUMENTS

| | | | |
|---|---|---|---|
| 4,501,907 | 2/1985 | Kwentus et al. | 549/259 |
| 4,567,158 | 1/1986 | Wrobleski et al. | 502/209 |
| 4,701,433 | 10/1987 | Edwards | 502/209 |
| 4,780,548 | 10/1988 | Edwards et al. | 549/259 |
| 4,855,459 | 8/1989 | Mummey | 549/260 |
| 5,117,007 | 5/1992 | Taheri | 549/259 |
| 5,185,455 | 2/1993 | Ebner | 549/259 |
| 5,631,387 | 5/1997 | Brown et al. | 549/259 |
| 5,877,331 | 3/1999 | Mummey et al. | 549/259 |
| 5,885,919 | 3/1999 | Bortinger | 502/209 |
| 5,895,817 | 4/1999 | Wagner | 546/286 |

*Primary Examiner*—Bernard Dentz
(74) *Attorney, Agent, or Firm*—Senniger Powers Leavitt & Roedel

(57) ABSTRACT

Improved methods and apparatus for the preparation of maleic anhydride by reacting a hydrocarbon having at least four carbon atoms in a straight chain with molecular oxygen in a catalytic reactor, the reactor comprising a fixed catalyst bed having active sites comprising a vanadium-phosphorus-oxygen catalyst for the catalytic oxidation of the hydrocarbon to maleic anhydride, said process further comprising the continuous or intermittent introduction of a phosphorus-containing agent to the reactor. The introduction of the phosphorus-containing agent into the maleic anhydride production system is controlled so to provide for a more uniform distribution of the phosphorus-containing agent throughout the reactor. The methods of the invention are effective to reduce deposits of the phosphorus-containing agent or decomposition products of the phosphorus-containing agent on reactor surfaces other than the catalytic bed thereby decreasing reactor maintenance and increasing reactor lifetime.

79 Claims, 4 Drawing Sheets

METHOD AND APPARATUS FOR IMPROVING THE UNIFORMITY OF DISTRIBUTION OF A PHOSPHORUS-CONTAINING AGENT THROUGHOUT A MALEIC ANHYDRIDE CATALYTIC REACTOR

CROSS-REFERENCE TO RELATED APPLICATION

This application claims priority from U.S. application Ser. No. 60/134,923 filed May 19, 1999.

BACKGROUND OF THE INVENTION

This invention relates to an improved process for the production of maleic anhydride by the oxidation of a hydrocarbon having at least four carbon atoms in a straight chain in a catalytic reactor. More particularly, this invention relates to a method for improving the uniformity of distribution of a phosphorus-containing agent throughout a maleic anhydride catalytic reactor.

Maleic anhydride is of significant commercial interest throughout the world. It is used alone or in combination with other acids in the manufacture of alkyd and polyester resins. It is also a versatile intermediate for chemical synthesis.

Maleic anhydride is conventionally manufactured by passing a gas comprising a hydrocarbon having at least four carbon atoms in a straight chain and oxygen through a catalyst bed, typically a fixed catalyst bed tubular plug flow reactor, containing a catalyst comprising mixed oxides of vanadium and phosphorus. The catalyst employed may further comprise promoters, activators or modifiers such as iron, lithium, zinc, molybdenum, chromium, uranium, tungsten, and other metals, boron and/or silicon. The reaction product gas produced contains maleic anhydride together with oxidation by-products such as carbon monoxide, carbon dioxide, water vapor, acrylic and acetic acids and other by-products, along with inert gases present in air when air is used as the source of molecular oxygen.

Because the reaction is highly exothermic, the reactor must be cooled during operation. Typically, a shell and tube heat exchanger is used as a reactor with the catalyst packed in the tubes through which the hydrocarbon and oxygen gases are passed. A cooling fluid, often a molten salt, flows over and cools the outside of the tubes. Because the length of the tubes is generally much greater than the diameter of the tubes, the reaction system approaches plug flow.

While the cooling capacity is substantially uniform throughout the reactor, the rate of reaction varies widely with the concentration of the hydrocarbon reactant and the temperature of the reaction zone. Because the reactant gases are generally at a relatively low temperature when they are introduced into the catalyst bed, the reaction rate is low in the region immediately adjacent the inlet of the reactor. Once the reaction begins, however, it proceeds rapidly with the rate of reaction further increasing as the reaction zone temperature increases from the heat released by the reaction. The reaction zone temperature continues to increase with distance along the length of the reactor tube until the depletion of the hydrocarbon causes the rate of reaction to decrease thereby decreasing the temperature of the reaction zone through transfer of heat to the cooling fluid, and allowing the remaining portion of the reactor tube to operate at a lower temperature differential. The point of maximum temperature reached in the reactor tube is generally referred to as the "hot spot".

If the temperature at the hot spot of the reactor becomes too great, problems can occur in the operation of the reactor. Generally, the selectivity of the catalyst varies inversely with the reaction temperature while the rate of reaction varies directly with the reaction temperature. Higher reaction zone temperatures result in lower catalyst selectivity and favor the complete oxidation of the hydrocarbon feedstock to carbon dioxide and water instead of maleic anhydride. As the hot spot temperature increases, the amount of the hydrocarbon feedstock consumed by the reaction increases but the decreased selectivity of the catalyst can result in a decreased yield of maleic anhydride. In addition, exposure of the catalyst bed to excessive temperatures may degrade the catalyst. Such degradation of the catalyst generally reduces the productivity of the operation and may also reduce the selectivity of the catalyst at a given temperature. Further, because the reaction rate constant increases exponentially with temperature, the reactor can experience thermal runaway if the temperature of the reactor becomes too high. The higher heat of reaction released by the conversion of the hydrocarbon feedstock to carbon dioxide and water further compounds this problem.

To modulate catalyst activity and enhance catalyst selectivity, a small amount of a phosphorus compound can be added to the reactant gases introduced to the reactor. Although the function of the phosphorus compound is not fully understood, it has been hypothesized that phosphorus is lost by the catalyst under the catalytic oxidation conditions and that a portion of the phosphorus compound added to the reactant gases is sorbed by the catalyst. It has been further hypothesized that this treatment of the catalyst with the phosphorus compound increases or restores the phosphorus/vanadium ratio of the catalyst to a ratio more favorable for catalyst selectivity, particularly a ratio that favors formation of maleic anhydride in preference to other catalytic by-products.

This treatment of the catalyst may be further modified by adding both water and a small amount of a phosphorus compound to the reactant gases introduced to the reactor. Although the function of this combination is not fully understood, it has been hypothesized that the addition of water to the reactor gases promotes a relatively even distribution of the sorbed phosphorus compound throughout the catalyst bed. In the absence of moisture, it has been observed that the phosphorus compound introduced into the reactant gases tends to deposit in an area immediately adjacent to the inlet of the tubular reactor.

Edwards, U.S. Pat. No. 4,701,433 and U.S. Pat. No. 4,810,803 disclose the introduction of water and a phosphorus compound into the catalyst bed of a maleic anhydride reactor to partially deactivate a portion of the catalyst bed and to make the temperature profile of the reactor more isothermal. Suitable phosphorus compounds are described to include alkyl phosphites and alkyl phosphates, including trimethyl phosphate. While Edwards discloses that the phosphorus compound and water can be added to the feedstock introduced to the reactor, he further discloses that a variety of other methods can be employed to add the phosphorus compound and water to the catalyst bed. These methods include the use of an aerosol to convey the phosphorus compound; the use of suspensions or colloidal solutions of the phosphorus compound; the use of a solvent for the phosphorus compound; and the addition of the phosphorus compound through a diluent gas such as nitrogen. Edwards does not, however, specifically teach how the phosphorus compound should be added to the feedstock or at what point in the process the phosphorus compound should be added to the feedstock.

Ebner, U.S. Pat. No. 5,185,455 discloses a process for controlling the rate of addition of trimethyl phosphate to an n-butane and oxygen stream entering a maleic anhydride catalytic reactor to improve catalyst selectivity without decreasing catalyst activity. Ebner describes a system for maintaining an optimal concentration of trimethyl phosphate in the reactant gases entering the reactor. Ebner, however, does not specifically teach how the trimethyl phosphate should be added to the feedstock or at what point in the process the trimethyl phosphate should be added to the feedstock.

SUMMARY OF THE INVENTION

Among the objects of the present invention, therefore, are the provision of an improved process for the production of maleic anhydride; a process for controlling the introduction of a phosphorus-containing agent into a maleic anhydride catalytic reactor; a process for improving the uniformity of distribution of a phosphorus-containing agent introduced into a maleic anhydride catalytic reactor throughout that reactor; a process for promoting vaporization and uniform distribution of a phosphorus-containing agent in a feed stream before the feed stream is introduced into a maleic anhydride catalytic reactor; and a process for reducing the accumulation of a phosphorus-containing agent (or decomposition products of a phosphorus-containing agent) on surfaces of a maleic anhydride catalytic reactor into which the phosphorus-containing agent is introduced.

It is a more particular object of the present invention to improve the uniformity of distribution of trimethyl phosphate in an n-butane and oxygen stream introduced into a maleic anhydride catalytic reactor thereby improving the uniformity of distribution of trimethyl phosphate throughout the reactor and/or reducing the accumulation of trimethyl phosphate (or decomposition products of trimethyl phosphate) on surfaces of a maleic anhydride catalytic reactor into which the trimethyl phosphate is introduced.

Other objects of the invention will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
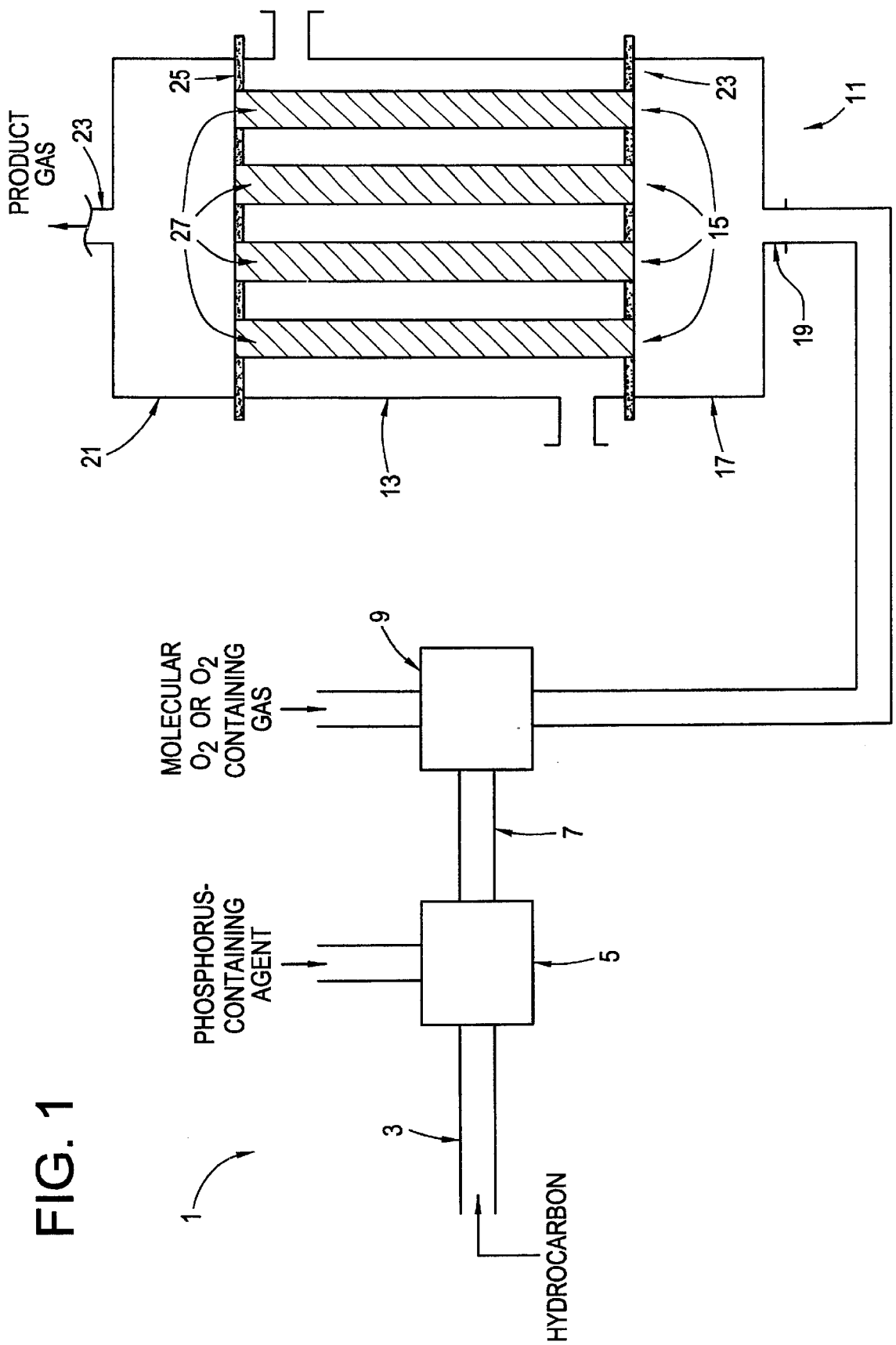
FIG. 1 is a schematic diagram of one embodiment of a process for the manufacture of maleic anhydride in accordance with the present invention.

Although it is known that a small amount of a phosphorus-containing agent can be added to the reactant gases introduced into a maleic anhydride catalytic reactor to modulate catalyst activity and enhance catalyst selectivity, the development of more active catalysts has necessitated the use of larger amounts of the phosphorus-containing agent to control hot spot activity in the reactor. As a result, significant deposition of the phosphorus-containing agent (or decomposition products of a phosphorus-containing agent) on reactor surfaces has occurred causing increased corrosion and pitting of those surfaces, particularly for reactor inlet tubesheets, inlet piping and rupture disc housings. Moreover, the distribution of phosphorus-containing agent deposits is uneven, with more of the phosphorus-containing agent flowing to the inlet and central portions of the tubesheet. Welding of tubesheet cracks caused by such depositions can result in considerable expense. Further, rate reduction due to resulting hot spot activity decreases the profitability of the process.

In accordance with the present invention, therefore, it has been discovered that the deposition and/or accumulation of a phosphorus-containing agent present in reactant gases introduced into a maleic anhydride catalytic reactor (or decomposition products of the phosphorus-containing agent) on the surfaces of the reactor can be materially reduced by improving the uniformity of distribution of the phosphorus containing agent in the reactant gases prior to introduction of the gases into the reactor. Improving the uniformity of distribution of such phosphorus containing agents or decomposition products of the phosphorus-containing agent can, for example, reduce unwanted pitting or corrosion of reactor surfaces, reduce required maintenance, and increase lifetime for the reactor.

Because poor distribution of the phosphorus-containing agent throughout a catalytic reactor used in the preparation of maleic anhydride also can result in some areas of the reactor receiving a less than normal, or less than optimal, amount of the phosphorus-containing agent and other areas of the reactor receiving a correspondingly greater than normal, or greater than optimal, amount of the phosphorus-containing agent, such nonuniform distribution of the phosphorus-containing agent throughout the reactor can have an adverse effect on the performance of the reactor. Improving the uniformity of distribution of such phosphorus containing agents or decomposition products of the phosphorus-containing agent can improve reactor performance.

In a tubular reactor where the phosphorus-containing agent is not uniformly distributed throughout the reactor, for example, the catalyst beds contained in those reactor tubes receiving a greater than normal amount of the phosphorus-containing agent exhibit increased deactivation although the operation of the tubes remains relatively stable. The hot spot of each tube shifts further into the catalyst bed but remains substantially well behaved. While the operation of these reactor tubes remains relatively stable, the conversion of the hydrocarbon feedstock introduced into those tubes generally decreases. In addition, although the catalyst beds contained in such tubes generally exhibit good selectivity, the maleic anhydride yield from these tubes decreases due to operating the reactor at less than the normal, or target, conversion. This decrease in conversion can be reversed, for example, by increasing the temperature at which the reaction is conducted. This increase in temperature, however, can lead to decreased catalyst selectivity (and thus increased production of carbon dioxide and water at the expense of maleic anhydride production) and accelerated degradation of the catalyst. Further, reactor tubes receiving a greater than normal amount of the phosphorus-containing agent may exhibit an increase in deposition of the phosphorus-containing agent or decomposition products of the phosphorus-containing agent on reactor or tube surfaces, particularly reactor inlet tubesheets, inlet piping and rupture disc housings.

In the illustrative tubular reactor, the catalyst beds contained in those reactor tubes receiving a less than normal amount of the phosphorus-containing agent are not deactivated to the same extent as catalyst beds receiving the normal amount of the phosphorus-containing agent. Operation of those tubes becomes less stable and more susceptible to thermal runaway in the catalyst bed under normal operating conditions. These tubes likewise are more sensitive to upsets from normal operation such as a decrease in space velocity. As the cooling fluid temperature is allowed to rise to increase the average reaction temperature, and thereby compensate for the decreased catalyst activity in the reactor tubes receiving a larger than normal amount of phosphorus-containing agent, the reactor tubes receiving a less than normal amount of phosphorus-containing agent operate at higher than target conversions of the hydrocarbon feedstock leading to decreased catalyst selectivity due to excessive hot spot temperatures in such tubes.

If the phosphorus-containing agent is not well-distributed throughout the reactor, the above problems may occur. The improved process in accordance with the present invention provides for a more consistent and uniform distribution of the phosphorus-containing agent introduced into the reactor and minimizes or eliminates such problems. In particular, the process in accordance with the present invention reduces the deposition or accumulation of solid or liquid phosphorus-containing agent or decomposition products of the phosphorus-containing agent on reactor surfaces other than the catalytic bed, particularly on reactor inlet surfaces, and more particularly on the rupture discs in the reactor inlet head. It is also hypothesized that the process in accordance with the present invention additionally provides one or more of the following beneficial effects relative to conventional processes: (1) a more consistent and uniform conversion of the hydrocarbon feedstock in the tubes; (2) a lower hot spot temperature in the tubes; (3) a slower increase in the temperature of the heat-transfer medium used to cool the reactor over time; (4) improved catalyst activity and/or stability, and/or (5) improved maleic anydride yield stability, i.e., a lower maleic anhydride yield decay value.

For purposes of this invention, the term "yield" means the ratio of the moles of maleic anhydride obtained to the moles of hydrocarbon feedstock introduced into the reaction zone multiplied by 100%, the term expressed in mole percent. The term "selectivity" means the ratio of moles of maleic anhydride obtained to the moles of hydrocarbon feedstock reacted or converted multiplied by 100, the term expressed in mole percent. The term "conversion" means the ratio of moles of hydrocarbon feed stock reacted to the moles of hydrocarbon feedstock introduced into the reaction zone multiplied by 100, the term expressed in mole percent. The term "space velocity" or "gas hourly space velocity" or "GHSV" means the hourly volume of gaseous feed expressed in cubic centimeters (cc) at 15.5° C. and atmospheric pressure, divided by the catalyst bulk volume, expressed in cubic centimeters, the term expressed as cc/cc-hr or $hr^{-1}$.

A schematic diagram of one embodiment of the process and apparatus of the present invention is illustrated in FIG. 1. The maleic anhydride production system in accordance with the present invention is generally designated by reference numeral 1. It will be understood by those skilled in the art that the present invention may be used in conjunction with catalytic reactors of various configurations and modes of operation, the following description is intended to be merely illustrative of the type of system in which the present invention may be applied.

A source of a hydrocarbon having at least four carbon atoms in a straight chain flows through a hydrocarbon feed line 3 to a first mixing zone 5. A phosphorus-containing agent is introduced into first mixing zone 5 to form a phosphorus-bearing hydrocarbon feed stream. The phosphorus-bearing hydrocarbon feed stream flows through a first conduit 7 to an oxygen mixing zone 9 wherein the phosphorus-bearing hydrocarbon feed stream is mixed with molecular oxygen or a molecular oxygen-containing gas to form a reactor feed gas. Oxygen mixing zone 9 is in fluid communication with tubular reactor 11 and the reactor feed gas flows from oxygen mixing zone 9 to tubular reactor 11 where it undergoes partial catalytic oxidation to maleic anhydride.

Tubular reactor 11 comprises a shell and tube heat exchanger having a shell 13, vertically oriented tubes 15, a lower head 17 having a gas inlet port 19, and an upper head having a lower gas exit port 21. Tubes 15 of the reactor are fixed in lower and upper tube sheets 23 and 25, and are packed with a catalyst to provide in each tube a component bed 27 of catalyst. Taken together, the combined tubes 15 constitute the reaction chamber. Inlet port 19 is in fluid flow communication with the reactor feed stream.

For phosphorus-containing agents that have a sufficient high vapor pressure under the applicable conditions, the introduction of the phosphorus-containing agent into the hydrocarbon feed stream preferably is controlled such that the phosphorus-containing agent is substantially vaporized in the reactor feed stream before the reactor feed stream enters the catalyst bed. More preferably, the introduction of the phosphorus-containing agent into the hydrocarbon feed stream is controlled such that at least about 90%, still more preferably at least about 95%, and still more preferably at least about 99%, of the phosphorus-containing agent is vaporized in the phosphorus-containing hydrocarbon feed stream prior to the combination of the phosphorus-containing hydrocarbon feed stream with molecular oxygen or molecular oxygen-containing gas, or at least before the reactor feed stream enters the catalyst bed.

In accordance with the instant invention, therefore, an improved process has been developed for the preparation of maleic anhydride by reacting a hydrocarbon having at least four carbon atoms in a straight chain with molecular oxygen in a catalytic reactor. The reactor generally comprises a fixed catalyst bed having active sites comprising a vanadium-phosphorus-oxygen catalyst for the catalytic oxidation of the hydrocarbon to maleic anhydride. A phosphorus-containing agent is continuously or intermittently introduced into the reactor. The manner in which the phosphorus-containing agent is introduced into the reactor is controlled so as to improve the distribution of the phosphorus-containing agent throughout the reactor.

In one embodiment of the invention, the phosphorus-containing agent is introduced into a gaseous feed stream comprising the hydrocarbon to provide a phosphorus-bearing hydrocarbon feed stream. The phosphorus-bearing hydrocarbon feed stream is combined with molecular oxygen or a molecular oxygen-containing gas to form a reactor feed stream. To achieve the desired distribution of the phosphorus-containing agent throughout the reactor, the introduction of the phosphorus-containing agent into the hydrocarbon feed stream is controlled such that the phosphorus-containing agent is substantially vaporized before the reactor feed stream enters the catalyst bed. The hydrocarbon is reacted with the molecular oxygen in the reactor to produce a reaction product comprising maleic anhydride.

To promote the desired vaporization and/or the substantially uniform distribution of the phosphorus-containing agent, the residence time of the phosphorus-containing agent in the phosphorus-bearing hydrocarbon feed stream prior to the combination of the phosphorus-bearing hydrocarbon feed stream with the molecular oxygen or molecular oxygen-containing gas preferably is greater than about three seconds, more preferably greater than about five seconds, and still more preferably greater than about eight seconds. Generally, a sufficient residence time of the phosphorus-containing agent in the phosphorus-bearing hydrocarbon feed stream prior to the combination of the phosphorus-bearing hydrocarbon feed stream with the molecular oxygen or molecular oxygen-containing gas is between about two seconds to about 90 seconds, preferably between about four seconds to about 30 seconds, more preferably between about six seconds to about 25 seconds, and still more preferably between about eight seconds to about 15 seconds.

While the above preferred residence times are expected to encompass most residence times that may be effectively employed in accordance with the present invention, those skilled in the art will recognize that residence times may vary from reactor to reactor depending upon parameters such as piping and reactor configuration and space velocity. For example, a reduction in the residence time of the phosphorus-containing agent in the phosphorus-bearing hydrocarbon feed stream prior to the combination of the phosphorus-bearing hydrocarbon feed stream with the molecular oxygen or molecular oxygen-containing gas may be acceptable in a given reactor configuration where there is an appropriate increase in the residence time of the reactor feed stream prior to introduction of the reactor feed stream into the reactor. Accordingly, the instant process should be interpreted broadly to include all residence times sufficient to allow the phosphorus-containing agent to be substantially vaporized and/or substantially uniformly distributed in the reactor feed stream before the reactor feed stream enters the catalyst bed.

In another embodiment, therefore, a phosphorus-containing agent is introduced into a gaseous feed stream comprising the hydrocarbon to provide a phosphorus-bearing hydrocarbon feed stream. The phosphorus-bearing hydrocarbon feed stream is combined with molecular oxygen or a molecular oxygen-containing gas to form a reactor feed stream. To achieve the desired vaporization and/or uniform distribution, the introduction of the phosphorus-containing agent into the hydrocarbon feed stream is controlled such that the phosphorus-containing agent is substantially uniformly distributed throughout the reactor feed stream before the reactor feed stream enters the catalyst bed. The hydrocarbon is reacted with the molecular oxygen in the reactor to produce a reaction product comprising maleic anhydride.

In still another embodiment, a phosphorus-containing agent is introduced into a feed stream comprising the hydrocarbon to provide a phosphorus-bearing hydrocarbon feed stream. The hydrocarbon feed stream is combined with molecular oxygen or a molecular oxygen-containing gas to form a reactor feed stream. To achieve the desired vaporization and/or uniform distribution, the introduction of the phosphorus-containing agent into the hydrocarbon feed stream is controlled such that the residence time of the phosphorus-containing agent in the phosphorus-bearing hydrocarbon feed stream prior to the combination of the phosphorus-bearing hydrocarbon feed stream with molecular oxygen or molecular oxygen-containing gas is greater than one second. The hydrocarbon is reacted with the molecular oxygen in the reactor to produce a reaction product comprising maleic anhydride.

In still another embodiment, the phosphorus-containing agent is introduced into a feed stream comprising the hydrocarbon in a first mixing zone to provide a phosphorus-bearing hydrocarbon feed stream. The phosphorus-bearing hydrocarbon feed stream passes through a conduit to an oxygen mixing zone and the phosphorus-bearing hydrocarbon feed stream is mixed with molecular oxygen or a molecular oxygen-containing gas in the oxygen mixing zone to form a reactor feed gas. The residence time of the phosphorus-bearing hydrocarbon feed stream in the conduit is greater than one second. The hydrocarbon is reacted with the molecular oxygen in the reactor to produce a reaction product comprising maleic anhydride.

Figure 2:
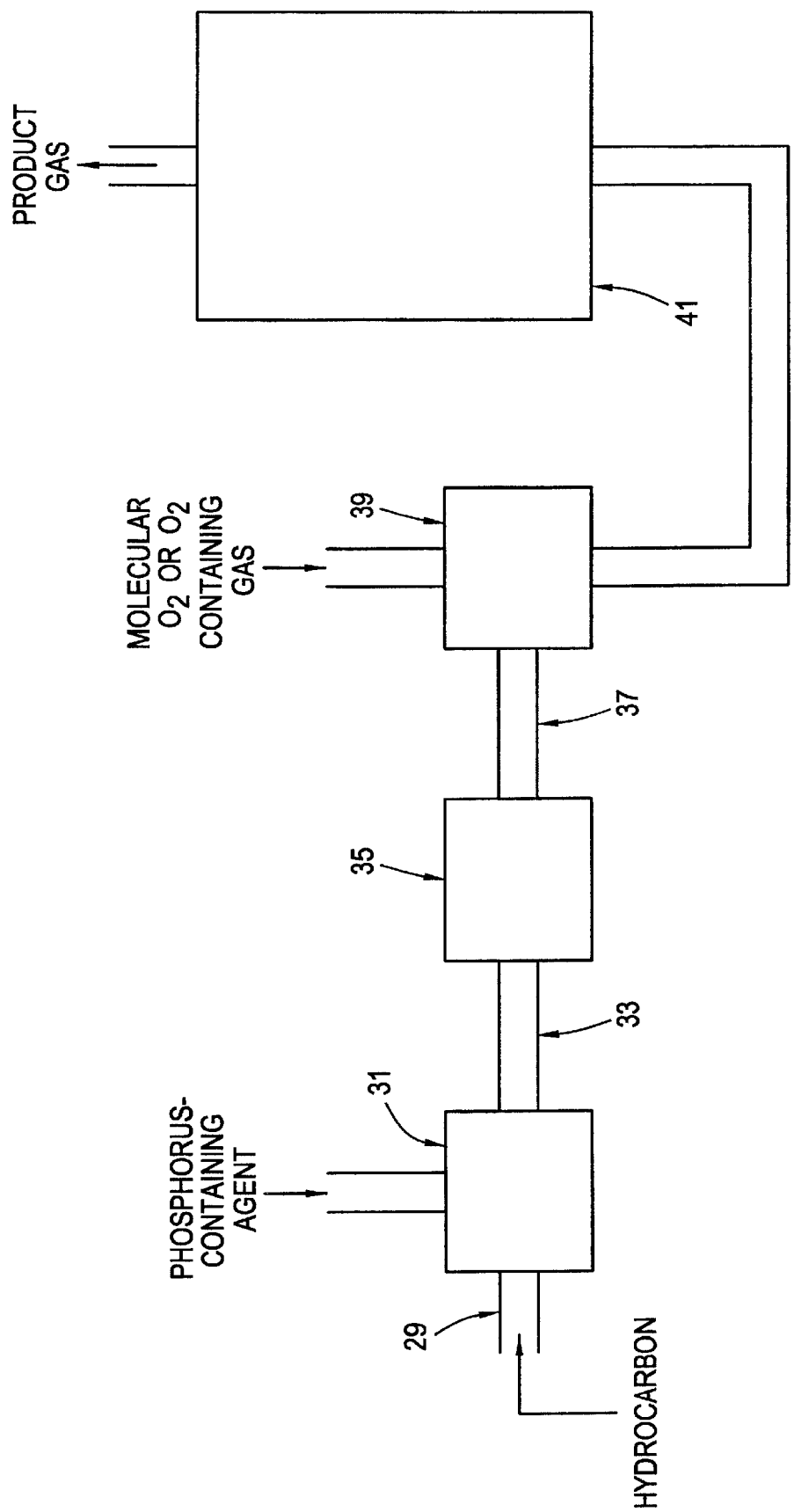
FIG. 2 is a schematic diagram of an alternative embodiment of the process for the manufacture of maleic anhydride shown in FIG. 1.

FIG. 2 illustrates an alternative embodiment of the process and apparatus of the present invention illustrated in FIG. 1. The maleic anhydride production system illustrated in FIG. 2 is largely the same as the maleic anhydride production system illustrated in FIG. 1 except that a gas/liquid contact zone is additionally incorporated in the system. In the system illustrated in FIG. 2, a source of a gaseous hydrocarbon having at least four carbon atoms in a straight chain flows through a hydrocarbon feed line 29 to a first mixing zone 31. A liquid phosphorus-containing agent is introduced into first mixing zone 31 to form a first phosphorus-bearing hydrocarbon feed stream. The first phosphorus-bearing hydrocarbon feed stream flows through a first conduit 33 to a gas/liquid contact zone 35 to form a second phosphorus-bearing hydrocarbon feed stream.

The second phosphorus-bearing hydrocarbon feed stream then flows through a second conduit 37 to an oxygen mixing zone 39 where the second phosphorus-bearing hydrocarbon feed stream is mixed with molecular oxygen or a molecular oxygen-containing gas to form a reactor feed gas. The reactor feed gas flows from oxygen mixing zone 39 to tubular reactor 41 where it undergoes partial catalytic oxidation to maleic anhydride.

The gas/liquid contact zone comprises a means for promoting interfacial contact between the liquid phosphorus-containing agent and the gaseous feed stream such as a means for reducing the average size of the liquid droplets entrained in the gaseous hydrocarbon feed by providing a surface area for impingement of the droplets, a means for promoting the uniform distribution of the liquid phosphorus-containing agent in the gaseous feed stream, and/or a means for promoting the vaporization of phosphorus-containing agent in the gaseous feed stream. More particularly, the means comprises a means selected, for example, from the group consisting of filter media, static mixers, pipe fittings and turbulence-inducing flow devices. The means preferably comprises a filter medium. Disposable and/or cartridge-type filter media, such as but not limited to pleated paper filters and wound fiber filters, are acceptable. When the means comprises a filter medium, the phosphorus-containing agent preferably is introduced upstream of the filter medium or is injected directly into the filter medium.

In another embodiment, therefore, a liquid phosphorus-containing agent is introduced into a gaseous feed stream comprising the hydrocarbon in a first mixing zone upstream of a gas/liquid contact zone to produce a phosphorus-bearing hydrocarbon feed stream. The gas/liquid contact zone comprises a means for promoting interfacial contact between the liquid phosphorus-containing agent and the hydrocarbon feed gas. The phosphorus-bearing hydrocarbon feed stream is combined with molecular oxygen or a molecular oxygen-containing gas downstream of the gas/liquid contact zone to form a reactor feed stream. The hydrocarbon is reacted with the molecular oxygen in the reactor to produce a reaction product comprising maleic anhydride.

In still another embodiment, a liquid phosphorus-containing agent is introduced into a gaseous feed stream comprising the hydrocarbon in a first mixing zone upstream of a gas/liquid contact zone to produce a phosphorus-bearing hydrocarbon feed stream. The gas/liquid contact zone comprises a means for promoting interfacial contact between the liquid phosphorus-containing agent and the hydrocarbon feed gas. The phosphorus-bearing hydrocarbon feed stream is combined with molecular oxygen or a molecular oxygen-containing gas downstream of the gas/liquid contact zone to form a reactor feed stream. The introduction of the phosphorus-containing agent into the hydrocarbon feed stream is controlled such that the residence time of the phosphorus-containing agent in the phosphorus-bearing hydrocarbon feed stream between the first mixing zone and the second mixing zone is greater than one second. The hydrocarbon is reacted with the molecular oxygen in the reactor to produce a reaction product comprising maleic anhydride.

In still another embodiment, a liquid phosphorus-containing agent is introduced into a gaseous feed stream comprising the hydrocarbon in a first mixing zone upstream of a filter medium through which the hydrocarbon feed stream is passed to provide a phosphorus-bearing hydrocarbon feed stream. The phosphorus-bearing hydrocarbon feed stream is combined with molecular oxygen or a molecular oxygen-containing gas in an oxygen mixing zone downstream of the filter medium. The hydrocarbon is reacted with the molecular oxygen in the reactor to produce a reaction product comprising maleic anhydride.

In still another embodiment, a liquid phosphorus-containing agent is introduced into a gaseous feed stream comprising the hydrocarbon in a first mixing zone upstream of a filter medium through which the hydrocarbon feed stream is passed to provide a phosphorus-bearing hydrocarbon feed stream. The phosphorus-bearing hydrocarbon feed stream is combined with molecular oxygen or a molecular oxygen-containing gas in an oxygen mixing zone downstream of the filter medium. The residence time of the phosphorus-bearing hydrocarbon feed stream between the first mixing zone and the oxygen mixing zone is greater than one second. The hydrocarbon is reacted with the molecular oxygen in the reactor to produce a reaction product comprising maleic anhydride.

For phosphorus-containing agents that remain substantially in liquid form prior to entering the reactor, the introduction of the phosphorus-containing agent into the hydrocarbon feed stream preferably is controlled such that the phosphorus-containing agent is substantially uniformly radially distributed in the reactor feed stream before the reactor feed stream enters the catalyst bed. In addition, the introduction of the phosphorus-containing agent into the hydrocarbon feed stream preferably is controlled such that the average particle size of the phosphorus-containing agent in the reactor feed stream is less than about $10\mu$, preferably less than about $5\mu$, and still more preferably between about $1\mu$ to $5\mu$.

In one embodiment, therefore, a phosphorus-containing agent is introduced into a gaseous feed stream comprising the hydrocarbon in a first mixing zone to provide a phosphorus-bearing hydrocarbon feed stream. The phosphorus-bearing feed stream passes through a filter medium that intercepts the liquid phosphorus-containing agent and distributes it within the medium laterally across the flow path of the hydrocarbon feed stream, thereby dispersing the phosphorus-containing agent to promote uniform radial distribution of the liquid phosphorus-containing agent within the phosphorus-bearing hydrocarbon stream as the liquid is re-entrained therein from the filter medium. The phosphorus-bearing hydrocarbon feed stream is combined with molecular oxygen or a molecular oxygen-containing gas in an oxygen mixing zone downstream of said filter medium. The hydrocarbon is reacted with the molecular oxygen in the reactor to produce a reaction product comprising maleic anhydride.

The liquid phosphorus-containing agent can be re-entrained in droplets presenting a high surface area effective to promote the vaporization of the droplets of the phosphorus-containing agent in the gas stream upon mixing with the oxygen-containing gas. The average particle size of such re-entrained droplets typically ranges between about 1 to about $5\mu$. The filter medium generally comprises a porous medium having an average pore size of between about 1 and about $10\mu$, preferably between about 1 and about $5\mu$, and preferably extends substantially across the entire flow path of the phosphorus-bearing hydrocarbon feed stream.

In still another embodiment, a phosphorus-containing agent is introduced into a gaseous feed stream comprising the hydrocarbon in a first mixing zone to provide a phosphorus-bearing hydrocarbon feed stream. The phosphorus-bearing feed stream is passed through a conduit comprising a flow restriction comprising means for dispersing the phosphorus-containing agent to promote uniform radial distribution of the phosphorus-containing containing agent within the phosphorus-bearing hydrocarbon stream. The phosphorus-bearing hydrocarbon feed stream is combined with molecular oxygen or a molecular oxygen-containing gas in an oxygen mixing zone downstream of said flow restriction comprising means. The hydrocarbon is reacted with the molecular oxygen in the reactor to produce a reaction product comprising maleic anhydride.

The flow restriction comprising means preferably comprises a gas/liquid contact zone comprising a means effective to promote interfacial contact between the liquid phosphorus-containing agent and the hydrocarbon gas. The passage of the phosphorus-bearing hydrocarbon feed stream through the gas/liquid contact zone preferably reduces the particle to size of the liquid droplets of the phosphorus-containing agent dispersed in the gaseous hydrocarbon, particularly to a size effective to promote vaporization of the liquid phosphorus-containing agent after the phosphorus-bearing hydrocarbon stream is mixed with the molecular oxygen or oxygen-containing gas. The gas/liquid contact zone can comprise, for example, impingement surfaces for the liquid droplets and/or a means for promoting vaporization of the droplets and can be selected, for example, from the group consisting of a filter medium, a static mixer, a pipe fitting and a turbulence inducing flow device.

In the various embodiments of the invention, a minimum residence time of the phosphorus-containing agent in the phosphorus-bearing hydrocarbon feed stream prior to the combination of the phosphorus-bearing hydrocarbon feed stream with the molecular oxygen or molecular oxygen-containing gas is not required so long as the gas/liquid contact zone, dispersing means, filter medium or the like causes or contributes to the phosphorus-containing agent being substantially vaporized and/or substantially uniformly distributed in the reactor feed stream before the reactor feed stream enters the catalyst bed. Preferably, however, a minimum residence time is provided in combination with a gas/liquid contact zone, dispersing means, filter medium or the like. The residence time of the phosphorus-containing agent in the phosphorus-bearing hydrocarbon feed stream prior to the combination of the phosphorus-bearing hydrocarbon feed stream with the molecular oxygen or molecular oxygen-containing gas preferably is greater than about three seconds, more preferably greater than about five seconds, and still more preferably greater than about eight seconds. Still more preferably, the residence time of the phosphorus-containing agent in the hydrocarbon feed stream prior to the combination of the phosphorus-bearing hydrocarbon feed stream with the molecular oxygen or molecular oxygen-containing gas is between about two seconds to about 90 seconds, preferably between about four seconds to about 30 seconds, more preferably between about six seconds to about 25 seconds, and still more preferably between about eight seconds to about 15 seconds.

The phosphorus-containing agent can be introduced by any suitable method. Methods providing greater dispersion of the phosphorus-containing agent in the hydrocarbon feed stream during the introduction of the agent, however, are preferred. The phosphorus-containing agent can be introduced into the hydrocarbon feed stream, for example, through a tube inserted into the hydrocarbon feed stream, wherein the tube comprises a fritted tip through which the phosphorus-containing agent exits the tube. In this example, the phosphorus-containing agent preferably is introduced into the hydrocarbon feed stream through a tube inserted into the hydrocarbon feed stream substantially perpendicular to the direction of the flow of the hydrocarbon feed stream, wherein the tube comprises a fritted tip through which the phosphorus-containing agent exits the tube.

The temperature of the hydrocarbon feed stream will depend upon the specific hydrocarbon selected. When the hydrocarbon is n-butane, the n-butane feed stream preferably is maintained at a temperature of at least about 70° C., preferably between about 70° C. to about 110° C., and more preferably between about 85° C. to about 95° C. The phosphorus-containing agent preferably is preheated before it is introduced into the hydrocarbon feed stream. While the phosphorus-containing agent can be at ambient temperature when introduced into the hydrocarbon feed stream, it preferably is preheated to a temperature no cooler than about 20° C. below, still more preferably no cooler than 10° C. below, the temperature of the hydrocarbon feed stream before it is introduced into the hydrocarbon feed stream. In one embodiment of the invention, the feed line carrying the phosphorus-containing agent is adjacent to, or wrapped around, the hydrocarbon feed line for an appropriate distance prior to introducing the agent into the hydrocarbon feed stream in order to elevate the temperature of the agent. In other embodiments, preheating is carried out, for example, using steam tracing or any other suitable method.

Similarly, each of the embodiments disclosed in the instant application can be further modified by introducing an additional amount of phosphorus-containing agent into the phosphorus-bearing hydrocarbon feed stream downstream from where a first amount of the phosphorus-containing agent is introduced into the hydrocarbon feed stream. The precise point in the process where the additional phosphorus-containing agent is introduced can vary. The additional phosphorus-containing agent may be introduced, for example, between the first mixing zone and the oxygen mixing zone, between the first mixing zone and the gas/liquid contact zone, or between the gas/liquid contact zone and the oxygen mixing zone. The additional phosphorus-containing agent preferably is introduced no later than immediately before the oxygen mixing zone. In embodiments employing divided process streams and a plurality of catalytic reactors, such as in the scheme depicted in FIG. 3 discussed below, the additional phosphorus-containing agent may be introduced, if desirable, into each divided phosphorus-containing hydrocarbon stream prior to the oxygen mixing zone for each separate reactor. This approach permits individual adjustment of the rate at which the phosphorus-containing agent is introduced to form the individual reactor feed streams for the various separate catalytic reactors employed. The phosphorus-containing agent is introduced at a first rate before the process stream is divided to provide a minimum concentration of the phosphorus-containing agent. Additional phosphorus-containing agent is introduced at a second rate after the process stream is divided to account for the individual characteristics of each separate reactor. In this manner, differences in the catalyst employed, the selectivity and activity of the catalyst and other operational differences for each reactor can be taken into account and the concentration of phosphorus-containing agent in the reactor feed gas adjusted to the target or optimum value for that reactor. Where additional phosphorus-containing agent is introduced downstream from the point in the process where the phosphorus-containing agent is first introduced, the ratio of the first rate of addition of the phosphorus-containing compound to the second rate of addition of the phosphorus-containing agent preferably is at least about 2:1, more preferably at least about 3:1, and still more preferably at least about 4:1.

In one embodiment, therefore, a phosphorus-containing agent is introduced into a feed stream comprising the hydrocarbon in a first mixing zone at a first rate to provide a first phosphorus-bearing hydrocarbon feed stream. The first phosphorus-bearing hydrocarbon feed stream passes through a first conduit to a second mixing zone. Additional phosphorus-containing agent is introduced into the first phosphorus-bearing hydrocarbon feed stream in a second mixing zone at a second rate to provide a second phosphorus-bearing hydrocarbon feed stream. The second phosphorus-bearing hydrocarbon feed stream passes through a second conduit to an oxygen mixing zone and where it is mixed with molecular oxygen or a molecular oxygen-containing gas in the oxygen mixing zone to form a reactor feed stream. The sum of the residence time of the first phosphorus-bearing hydrocarbon feed stream between the first mixing zone and the second mixing zone and the residence time of the second phosphorus-bearing hydrocarbon feed stream between the second mixing zone and the oxygen mixing zone is greater than one second. The hydrocarbon is reacted with the molecular oxygen in the reactor to produce a reaction product comprising maleic anhydride.

Figure 3:
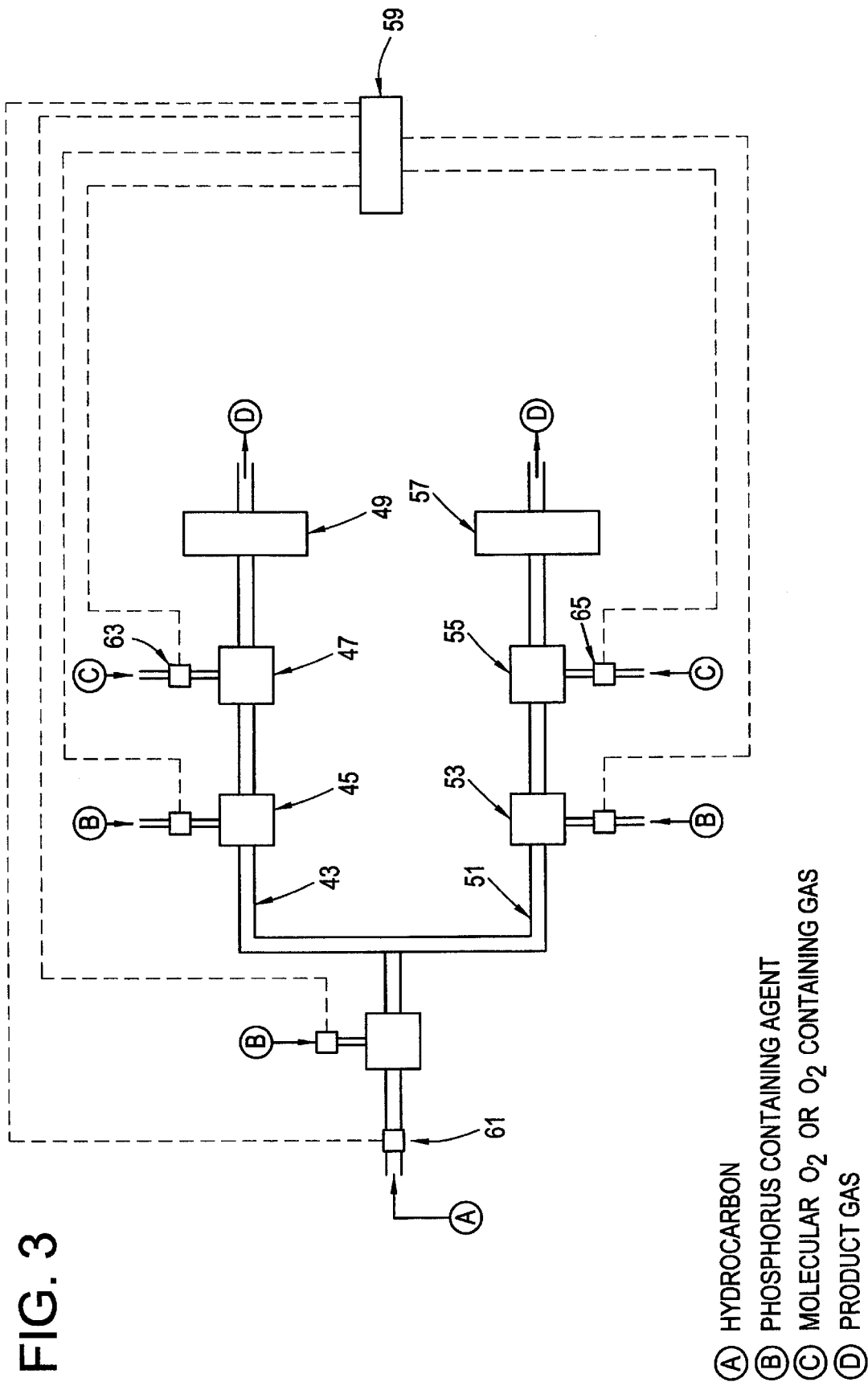
FIG. 3 is a schematic diagram of still another embodiment of a process for the manufacture of maleic anhydride in accordance with the present invention wherein a phosphorus-bearing hydrocarbon feed stream is divided and directed to a plurality of maleic anhydride catalytic reactors.
Figure 4:
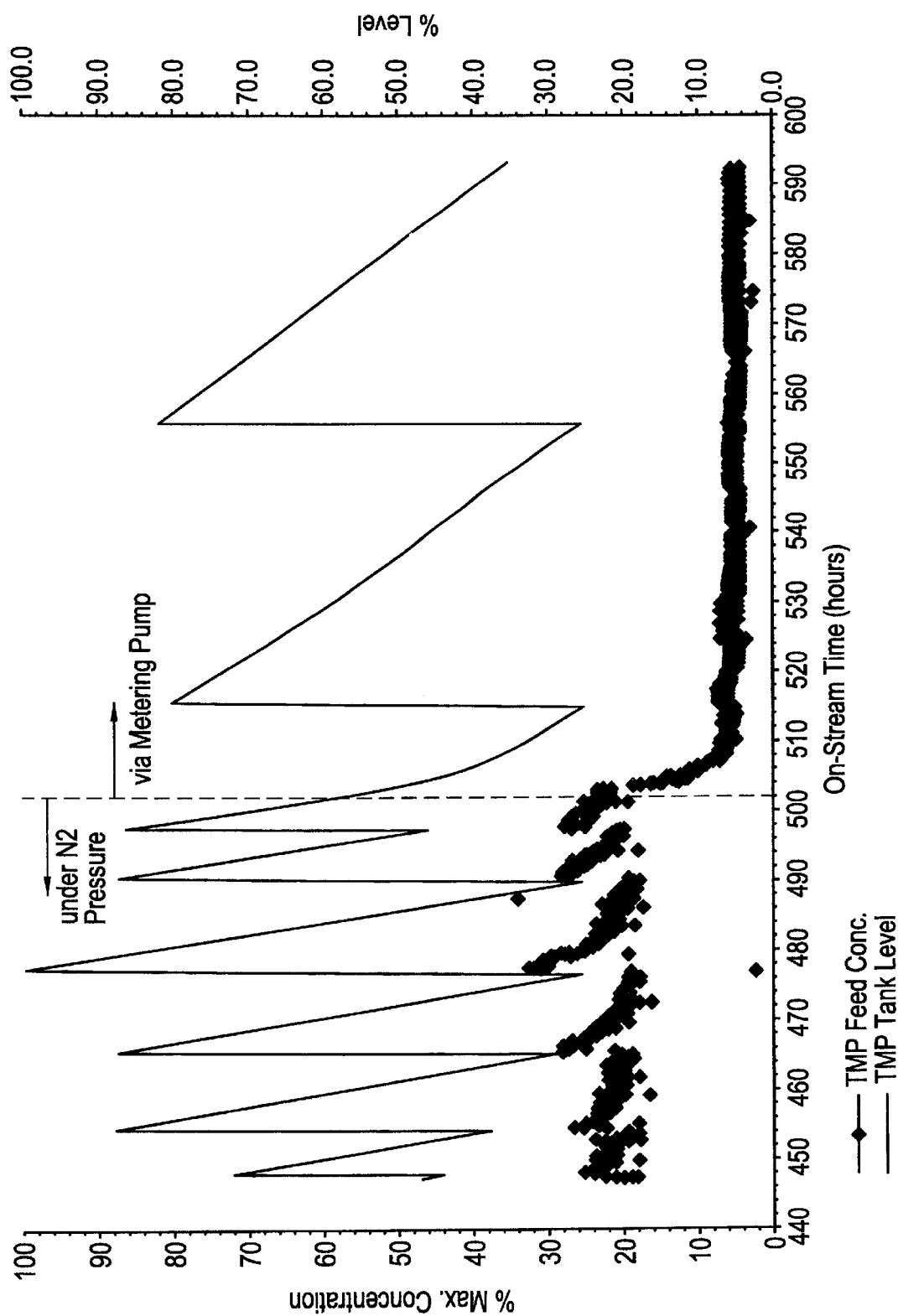
FIG. 4 shows a plot comparing the standard deviation of trimethyl phosphate concentration in the reactor feed stream as a function of time for (a) trimethyl phosphate addition controlled by metering pump, and (b) trimethyl phosphate addition controlled by pressurized nitrogen feed tank.

FIG. 3 illustrates still another alternative embodiment of the process and apparatus of the present invention wherein a hydrocarbon feed stream comprising the phosphorus-containing agent is divided and directed to a plurality of maleic anhydride catalytic reactors. The maleic anhydride production system illustrated in FIG. 3 is similar to the maleic anhydride production system illustrated in FIG. 1 except that the phosphorus-bearing hydrocarbon stream is divided into a plurality of divided phosphorus-bearing hydrocarbon feed streams prior to reaching oxygen mixing zone 33 shown in FIG. 1 and an additional mixing zone wherein additional phosphorus-containing agent is introduced into each divided stream is incorporated in the scheme. In FIG. 3 two divided streams (a first reactor hydrocarbon feed stream and a second reactor hydrocarbon feed stream) are shown for purposes of illustrating this embodiment although additional divided streams are possible.

A first reactor hydrocarbon feed stream flows through a first reactor hydrocarbon feed line 43 to a first reactor mixing zone 45 where additional phosphorus-containing compound is optionally introduced into the first reactor hydrocarbon feed stream at a first reactor rate to form a first reactor phosphorus-bearing hydrocarbon feed stream. The first reactor phosphorus-bearing hydrocarbon feed stream then flows to a first reactor oxygen mixing zone 47 and is mixed with molecular oxygen or a molecular oxygen-containing gas to form a first reactor feed gas. The first reactor feed gas flows from first reactor oxygen mixing zone 47 to a first tubular reactor 49 where it undergoes partial catalytic oxidation to maleic anhydride.

Similarly, a second reactor hydrocarbon stream flows through a second reactor hydrocarbon feed line 51 to a second reactor mixing zone 53 where additional phosphorus-containing compound is optionally introduced into the second reactor hydrocarbon feed stream at a second reactor rate to form a second reactor phosphorus-bearing hydrocarbon feed stream. The second reactor phosphorus-bearing hydrocarbon feed stream then flows to a second reactor oxygen mixing zone 55 and is mixed with molecular oxygen or a molecular oxygen-containing gas to form a second reactor feed gas. The second reactor feed gas flows from second reactor oxygen mixing zone 55 to a second tubular reactor 57 where it undergoes partial catalytic oxidation to maleic anhydride.

The rate at which phosphorus-containing agent is introduced to each of the mixing zones is controlled by one or more controller means 59 that receive information from flow measurement means 61, 63 and 65. Controller means 59 preferably is a PID-type controller. Flow measurement means 61 measures the flow rate of the hydrocarbon feed stream before division of that stream. Flow measurement means 63 measures the flow rate of the oxygen or oxygen-containing feed stream that is introduced into the first reactor oxygen mixing zone. Flow measurement means 65 measures the flow rate of the oxygen or oxygen-containing feed stream that is introduced into the second reactor oxygen mixing zone. Set-points corresponding to the target concentration of the phosphorus-containing agent in the first reactor feed stream and the target concentration of the phosphorus-containing agent in the second reactor feed stream are inputted to controller means 59. These set-points typically are determined by the operator or a supervisory computer based on an evaluation of, for example, maleic anhydride yield, hot spot temperature and other parameters specific to each reactor. A set-point corresponding to a target ratio of phosphorus-containing agent introduced in the first mixing zone (before the streams are divided) to total phosphorus-containing agent introduced in the overall system is then inputted to controller means 59.

In operation controller means 59 receives hydrocarbon and oxygen flow information from flow measurement means 61, 63 and 65 and then (1) calculates the rate (as a function of the measured flow rates) at which the phosphorus-containing agent must be introduced to reach the lower of the two concentration set-points for the first reactor feed stream and the second reactor feed stream, and (2) reduces this calculated rate in accordance with the ratio set-point to determine the first rate for the phosphorus-containing agent to be introduced to the first mixing zone. Controller means 59 then regulates the introduction of the phosphorus-containing agent into the first mixing zone in accordance with the calculated first rate.

Controller means 59 then calculates the rate (as a function of the hydrocarbon and oxygen flow rates) at which additional phosphorus-containing agent must be introduced into the first reactor hydrocarbon feed stream to reach the concentration set-point specified for the first reactor feed stream. Similarly, controller means 59 then calculates the rate (as a function of the hydrocarbon and oxygen flow rates) at which additional phosphorus-containing agent must be introduced into the second reactor hydrocarbon feed stream to reach the concentration set-point specified for the second reactor feed stream. Controller means 59 then regulates the introduction of the phosphorus-containing agent into the first reactor mixing zone and the second reactor mixing zone in accordance with the calculated first reactor rate and second reactor rate, as appropriate.

One skilled in the art will appreciate that the scheme depicted in FIG. 3 can be successfully modified by dividing the reactor feed stream into a plurality of reactor feed streams that are introduced into separate catalytic reactors instead of dividing the phosphorus-bearing hydrocarbon stream as shown in FIG. 3. The divided reactor feed streams can, but need not, have equivalent flow volumes. These flow volumes can be adjusted to account for differences in the capacity in the reactors employed.

In one embodiment, therefore, a supply of phosphorus-containing agent is divided between a primary supply for delivery to a primary mixing zone and a secondary supply for delivery to a secondary mixing zone downstream of said primary mixing zone with respect to the flow of hydrocarbon gas to said reactor. The rate of flow of hydrocarbon gas entering the primary mixing zone is measured. The primary supply of phosphorus-containing agent is introduced into the hydrocarbon gas in the primary mixing zone to provide a primary phosphorus-bearing hydrocarbon stream. The rate at which the primary supply of phosphorus-containing agent is introduced into the primary mixing zone is controlled based on the measured hydrocarbon gas flow rate to provide a predetermined minimum concentration of the phosphorus-containing agent in the primary phosphorus-bearing hydrocarbon stream exiting the primary mixing zone.

The secondary supply of phosphorus-containing agent is introduced into the primary phosphorus-bearing hydrocarbon stream in the secondary mixing zone to produce an adjusted phosphorus-bearing hydrocarbon stream. The rate at which the secondary supply of said phosphorus-containing agent is introduced into the secondary mixing zone is controlled to provide a total concentration of phosphorus-containing agent in said adjusted phosphorus-bearing hydrocarbon stream corresponding to a predetermined concentration having a hydrocarbon to phosphorus-containing compound ratio effective to provide a target concentration of phosphorus in said reactor feed gas entering said catalyst bed. The adjusted phosphorus-bearing hydrocarbon feed stream is mixed with an oxygen-containing gas to provide the reactor feed stream. The hydrocarbon is reacted with the molecular oxygen in the reactor to produce a reaction product comprising maleic anhydride.

The phosphorus-bearing hydrocarbon stream exiting the primary mixing zone and the secondary supply of the phosphorus-containing agent can each be divided into a plurality of secondary streams for separate supply to a plurality of secondary mixing zones downstream of the primary mixing zone, and the adjusted phosphorus-bearing hydrocarbon feed stream exiting each of the secondary mixing zones can be delivered to a corresponding reactor of a plurality of reactors each supplied from a separate secondary mixing zone. The concentration of phosphorus-containing agent in the phosphorus-bearing hydrocarbon stream exiting the primary mixing zone preferably is equal to or lower than a predetermined concentration having a hydrocarbon to phosphorus-containing compound ratio effective to provide the lowest of the target concentrations of phosphorus in the reactor feed gases respectively entering the catalyst beds of said plurality of reactors. Still more preferably, the rate of introduction of the phosphorus-containing compound into each of the plurality of secondary mixing zones is controlled to provide a predetermined concentration having a hydrocarbon to phosphorus-containing compound ratio effective to provide a target concentration of phosphorus in the reactor feed gas entering the catalyst bed to which the stream exiting such secondary mixing zone is directed.

In still another embodiment, a supply of phosphorus-containing agent is divided between a primary supply for delivery to a primary mixing zone and a secondary supply for delivery to a secondary mixing zone downstream of the primary mixing zone with respect to the flow of hydrocarbon gas to the reactor. The rate of flow of hydrocarbon gas entering the primary mixing zone is measured. The primary supply of the phosphorus-containing agent is introduced into the hydrocarbon gas in the primary mixing zone to provide a primary phosphorus-bearing hydrocarbon stream. The rate at which the primary supply of the phosphorus-containing agent is introduced into the primary mixing zone is controlled based on the measured hydrocarbon gas flow to provide a predetermined minimum concentration of the phosphorus-containing agent in the primary phosphorus-bearing hydrocarbon stream exiting the primary mixing zone.

The secondary supply of the phosphorus-containing agent and another stream comprising the primary phosphorus bearing hydrocarbon stream are introduced into the secondary mixing zone to produce an adjusted phosphorus-bearing stream. The rate of introduction of the secondary supply of the phosphorus-containing agent into the secondary mixing zone is controlled to provide a total concentration of phosphorus-containing agent in the adjusted phosphorus-bearing hydrocarbon stream corresponding to a predetermined concentration having a hydrocarbon to phosphorus-containing compound ratio effective to provide a target concentration of phosphorus in the reactor feed gas entering the catalyst bed.

The primary phosphorus-bearing hydrocarbon stream preferably is mixed with phosphorus-containing agent introduced into the secondary mixing zone. Still more preferably, the primary phosphorus-bearing hydrocarbon stream is mixed with an oxygen containing gas to produce a pre-adjusted reactor feed gas with the pre-adjusted reactor feed gas being mixed with phosphorus-containing agent introduced into the secondary mixing zone to produce an adjusted reactor feed stream.

In still another embodiment, involving the operation of a plurality of catalytic reactors for preparing maleic anhydride by reacting a hydrocarbon having at least four carbon atoms in a straight chain with molecular oxygen, each reactor comprising a fixed catalyst bed having active sites comprising a vanadium-phosphorus-oxygen catalyst for the catalytic oxidation of the hydrocarbon to maleic anhydride, the improved process is directed to controlling the continuous or intermittent introduction of a phosphorus-containing agent into the reactor. The flow rate of a feed stream comprising the hydrocarbon is measured. A first rate of addition of the phosphorus-containing agent to be introduced into the hydrocarbon feed stream is calculated. The introduction of the phosphorus-containing agent into the hydrocarbon feed stream is controlled in accordance with the calculated first rate of addition. The first rate of addition corresponds to a minimum predetermined rate of addition of the phosphorus-containing agent as a function of the measured flow rate of the hydrocarbon feed stream. The phosphorus-containing agent is introduced into the hydrocarbon feed stream in a first mixing zone to provide a primary phosphorus-bearing hydrocarbon feed stream. The primary phosphorus-bearing hydrocarbon feed stream passes through a first conduit to a manifold where the primary phosphorus-bearing hydrocarbon feed stream is divided into a plurality of secondary hydrocarbon feed streams passing through a series of second conduits to a series of second mixing zones.

A second rate of addition of the phosphorus-containing agent to be optionally introduced into each secondary hydrocarbon feed stream is calculated. The introduction of the phosphorus-containing agent into each secondary hydrocarbon feed stream is controlled in accordance with each corresponding calculated second rate of addition. The second rate of addition of the phosphorus-containing agent introduced into each secondary hydrocarbon feed stream is independent of the second rate of addition of the phosphorus-containing agent introduced into each of the other secondary hydrocarbon feed streams. The second rate of addition is calculated for each secondary hydrocarbon feed stream as a function of the measured flow rate of the hydrocarbon feed stream and corresponds to a final target rate of addition of phosphorus-containing agent for the reactor into which the secondary reactor feed stream is to be introduced as reduced to account for the portion of the phosphorus-containing agent previously introduced in the first mixing zone that is contained in the secondary reactor feed stream. The phosphorus-containing agent is optionally introduced into each secondary hydrocarbon feed stream in each second mixing zone to provide a plurality of secondary phosphorus-bearing hydrocarbon feed streams. Each secondary phosphorus-bearing hydrocarbon feed stream is mixed with molecular oxygen or a molecular oxygen-containing gas in an oxygen mixing zone to produce a plurality of secondary reactor feed streams that are introduced into separate catalytic reactors. The sum of the residence time of the primary phosphorus-bearing hydrocarbon feed stream between the first mixing zone and the manifold, the residence time of the secondary hydrocarbon feed stream between the manifold and the second mixing zone, and the residence time of the secondary phosphorus-bearing hydrocarbon feed stream between the second mixing zone and the oxygen mixing zone is greater than one second. The hydrocarbon is reacted with the molecular oxygen in each catalytic reactor to produce a reaction product comprising maleic anhydride.

In still another embodiment, the flow rate of a feed stream comprising the hydrocarbon is measured. A first rate of addition of phosphorus-containing agent to be introduced into the hydrocarbon feed stream is calculated. The introduction of the phosphorus-containing agent into the hydrocarbon feed stream is controlled in accordance with the calculated first rate of addition. The first rate of addition corresponds to a minimum predetermined rate of addition of the phosphorus-containing agent as a function of the measured flow rate of the hydrocarbon feed stream. The phosphorus-containing agent is introduced into the hydrocarbon feed stream in a first mixing zone to provide a first phosphorus-bearing hydrocarbon feed stream. The first phosphorus-bearing hydrocarbon feed stream passes through a first conduit to a second mixing zone.

A second rate of addition of phosphorus-containing agent to be optionally introduced into the first phosphorus-bearing hydrocarbon feed stream is calculated. The introduction of the phosphorus-containing agent into the first phosphorus-bearing hydrocarbon feed stream is controlled in accordance with the calculated rate of addition. The second rate of addition is calculated as a function of the measured flow rate of the hydrocarbon feed stream and corresponds to a final target rate of addition of phosphorus-containing agent for the reactor as reduced to account for the phosphorus-containing agent previously introduced in the first mixing zone. The phosphorus-containing agent is introduced into the first phosphorus-bearing hydrocarbon feed stream in the second mixing zone to provide a second phosphorus-bearing hydrocarbon feed stream. The second phosphorus-bearing hydrocarbon feed stream is combined with molecular oxygen or a molecular oxygen-containing gas in an oxygen mixing zone to form a reactor feed stream. The sum of the residence time of the first phosphorus-bearing hydrocarbon feed stream between the first mixing zone and the second mixing zone and the residence time of the second phosphorus-bearing hydrocarbon feed stream between the second mixing zone and the oxygen mixing zone is greater than one second. The hydrocarbon is reacted with the molecular oxygen in the reactor to produce a reaction product comprising maleic anhydride.

Each of the embodiments discussed above with respect to FIG. 3 can be further modified to incorporate one or more gas/liquid contact zones in the same manner as discussed for the scheme of FIG. 2 at a position or positions between the first mixing zone and the diverted mixing zones.

The catalytic reactors that may be employed in accordance with the present invention broadly encompass any reactor that may be employed to convert hydrocarbons having at least four carbon atoms in a straight chain to maleic anhydride. A typically satisfactory reactor is a heat transfer medium-cooled fixed bed tube-type reactor. The details of operation of such reactors are well known to those skilled in the art. The tubes of such reactors can be constructed of iron, stainless steel, carbon steel, nickel, glass, such as Vycor, and the like. The tubes can vary in diameter from about 0.635 cm (0.25 in.) to about 3.81 cm (1.50 in.), and in length from about 15.24 (6 in.) to about 609.60 cm (20 ft). The oxidation reaction is highly exothermic and once the reaction is underway, in order to maintain the desired reaction zone temperature, a heat transfer medium is necessary to conduct heat away from the reaction zone. Suitable heat transfer media are well known to those skilled in the art and, in general, are materials that remain in the liquid state at process temperatures and have a relatively high thermal conductivity. Examples of useful media include various heat transfer oils, molten sulfur, mercury, molten lead, and salts such as nitrates and nitrites of alkali metals, the salts being preferred due to their high boiling points. A particularly preferred heat transfer medium is a eutectic mixture of potassium nitrate, sodium nitrate and sodium nitrite which not only has a desirably high boiling point, but also, a sufficiently low freezing point that it remains in a liquid state even during periods of reaction zone shutdown. An additional method of temperature control is to use a metal block reactor whereby the metal surrounding the reaction zone acts as a temperature regulating body or by conventional heat exchangers.

In general, operations in accordance with the instant invention involve charging a mixture of hydrocarbon having at least four carbon atoms in a straight chain with a molecular oxygen-containing gas (including molecular oxygen), such as air, to a heat transfer medium cooled reaction zone packed with the catalyst and contacting the catalyst with the hydrocarbon-molecular oxygen-containing gas mixture to produce a reaction product gas containing maleic anhydride.

Reaction temperature typically is maintained at about 300° C. to about 600° C., and preferably about 325° C. to about 500° C. The temperature of the reactor will depend to some extent, for example, upon the type of the reactor and the concentrations of the hydrocarbon and the phosphorus-containing agent in the reactor feed stream. The cooling bath for the reactor typically is maintained at a lower temperature that is sufficient to maintain the reaction temperature within the desired range.

Reaction pressure is not narrowly critical. The reaction may be conducted at atmospheric, superatmospheric or subatmospheric pressures. It generally will be preferred, however, for practical reasons, to conduct the reaction at or near atmospheric pressure. Typically, pressures of from about 14.7 psig to about 50.0 psig, more preferably about 16.0 psig to about 30.0 psig, and still more preferably about 18.0 psig to about 28.0 psig may be conveniently employed. The exit pressure will be at least slightly higher than ambient pressure to ensure a positive flow from the reactor. The pressure of the inert gases must be sufficiently higher to overcome the pressure drop through the reactor.

Hydrocarbon concentrations in the reactor feed stream typically range from about 1 mole percent to about 10 mole percent, preferably about 1.5 mole percent to about 5 mole percent.

The temperature of the molecular oxygen or molecular oxygen-containing gas that is mixed with the hydrocarbon typically is at least about 120° C., and preferably ranges from about 120° C. to about 200° C., more preferably from about 130° C. to about 180° C., and still more preferably from about 140° C. to about 160° C.

Gas hourly space velocity ("GHSV") for the process typically ranges from about 100 hr$^{-1}$ to about 4000 hr$^{-1}$, preferably about 1000 hr$^{-1}$ to about 3000 hr$^{-1}$, and more preferably about 1700 hr$^{-}$to about 2500 hr$^{-1}$.

Catalysts suitable for use in the instant invention are those known in the art, and in general, are materials capable of catalyzing the vapor phase partial oxidation of hydrocarbon having at least four carbon atoms in a straight chain to maleic anhydride under oxidation conditions. Examples of useful catalysts include a vanadium-phosphorus-oxide catalyst sold by Huntsman Corporation under the trade designation E326 activated in the manner described and claimed in U.S. Pat. No. 5,137,860; a vanadium-phosphorus-oxide catalyst described and claimed in U.S. Pat. No 4,632,915 or U.S. Pat. No. 4,670,415 and sold by Huntsman Corporation under the trade designation E307; and a modified vanadium-phosphorus-oxide catalyst sold by Huntsman Corporation under the trade designation E326 which is air calcined and activated in the presence of nitrogen and steam; the catalysts disclosed in Andrews et al., U.S. Pat. No. 5,275,996; Mitchell et al., U.S. Pat. No. 5,641,722; and Mitchell et al., U.S. Pat. No. 5,773,382 (particularly those catalysts sold by Huntsman Corporation under the trade designation E400); and the catalysts disclosed in U.S. patent application Ser. No. 08/538,005 filed Oct. 2, 1995 now U.S. Pat. No. 5,945,368; and U.S. patent application Ser. No. 08/909,638 filed Aug. 12, 1997 now U.S. Pat. No. 5,929,256 (particularly those catalysts sold by Huntsman Corporation under the trade designation E358). It should be understood, however, that these examples are not to be construed as limiting but instead are for purposes of illustration and guidance in the practice of the instant invention. In general, the atomic ratio of vanadium to phosphorus for these catalysts can suitably be in the range of about 0.5:1 to about 1.25:1, preferably in the range of about 0.95:1 to about 1.2:1. Among such catalysts, preferred catalyst include those catalysts sold by Huntsman Corporation under the trade designations E400 and E358.

In the process of the instant invention, the catalyst can be employed in one or more fixed beds. The size and shape of such fixed bed in not narrowly critical. For example, the catalyst can be in the shape of a cylinder, either solid or hollow, or any other suitable shape.

Phosphorus-containing agents suitable for use in the instant invention are those known in the art, and in general, are materials capable of modulating catalyst activity and/or enhancing selectivity of the catalyst when incorporated in the reactor feed stream. Non-limiting examples of usefull catalysts are those described in U.S. Pat. No. 4,701,433, it being understood, however, that the same are not to be construed as limiting but instead are for purposes of illustration and guidance in the practice of the instant invention.

Among such phosphorus-containing agents, those preferred for use according to the instant invention comprise an alkyl ester of orthophosphoric acid or an alkyl ester of an orthophosphoric acid derivative. Preferably, the phosphorus-containing agent comprises an alkyl ester of orthophosphoric acid having the following structure:

$(RO)_3P=O$                         (I)

or an alkyl ester of an orthophosphoric acid derivative having the following structure:

$(RO)_3P$                             (II)

wherein R is hydrogen or a $C_1$ to $C_4$ alkyl, at least one R being a $C_1$ to $C_4$ alkyl. More preferably, the phosphorus-containing agent comprises a compound selected from the group consisting of trialkyl phosphates and trialkyl phosphites. Still more preferably, the phosphorus-containing agent comprises a compound selected from the group consisting of trimethyl phosphate, triethyl phosphate, trimethyl phosphite and triethyl phosphite. Still more preferably, the phosphorus-containing agent is trimethyl phosphate.

The phosphorus-containing agent concentration in the reactor feed stream is preferably at least about 1 ppmw, preferably between about 1 ppmw to about 20 ppmw, more preferably between about 4 ppmw to about 17 ppmw, and still more preferably, about 7 ppmw to about 14 ppmw. The introduction of the phosphorus-containing agent can be continuous or intermittent, preferably continuous. The rate at which the phosphorus-containing agent is introduced into the catalytic reactor generally is between about 0.005 g per kilogram of total bed catalyst per day to about 5 g per kilogram of the total catalyst in the bed per day.

A large number of hydrocarbons having from four to 10 carbon atoms can be converted to maleic anhydride in the process of the present invention. It is only necessary that the hydrocarbon contain not less than four carbon atoms in a straight chain. As an example, the saturated hydrocarbon n-butane is satisfactory, but isobutane (2-methyl propane) is not satisfactory for conversion to maleic anhydride although its presence is not harmful. In addition to n-butane, other suitable saturated hydrocarbons include the pentanes, the hexanes, the heptanes, the octanes, the nonanes, the decanes, and mixtures of any of these, with or without n-butane, so long as a hydrocarbon chain having at least four carbon atoms in a straight chain is present in the saturated hydrocarbon molecule.

Unsaturated hydrocarbons are also suitable for conversion to maleic anhydride in accordance with the process of the present invention. Suitable unsaturated hydrocarbons include the butenes (1-butene and 2-butene), 1,3-butadiene, the pentenes, the hexenes, the heptenes, the octenes, the nonenes, the decenes and mixtures of any of these, again, so long as the requisite hydrocarbon chain having at least four carbon atoms in a straight chain is present in the molecule.

Cyclic compounds such a cyclopentane and cyclopentene are also satisfactory feed materials for conversion to maleic anhydride.

Of the aforementioned feedstocks, n-butane is the preferred saturated hydrocarbon and the butenes are the preferred unsaturated hydrocarbons, with n-butane being more preferred. It will be noted that the aforementioned feedstocks need not necessarily be pure substances, but can be technical grade hydrocarbons.

The principal product from the oxidation of the aforementioned suitable feed materials is maleic anhydride, although small amounts of methyl maleic anhydride may also be produced when the feedstock is a hydrocarbon containing more than four carbon atoms. Maleic anhydride produced in accordance with the process of the present invention can be recovered by any means known to those skilled in the art. For example, maleic anhydride can be recovered by direct condensation or by absorption in suitable media with subsequent separation and purification of the anhydride.

Typical average values for conversion of the hydrocarbon feed to the reactor are at least about 60%, preferably about 60% to about 90%, more preferably about 70% to about 85%, and still more preferably about 80% to about 85%.

Typical average values for the established initial maleic anhydride yield are at least about 40 mole percent, preferably at least about 45 mole percent, and more preferably at least about 47 mole percent.

In general, the improved process exhibits an average yield decay of less than about 0.25% per month, preferably less than about 0.15%, and more preferably less than about 0.125%.

The present invention is illustrated by the following examples which are merely for the purpose of illustration and are not to be regarded as limiting the scope of the invention or the manner in which it is practiced.

EXAMPLE 1

REDUCTION IN TRIMETHYL PHOSPHATE DEPOSITS

A multi-tubular fixed-bed catalytic reactor was operated to prepare maleic anhydride from a reactor feed stream comprising n-butane in air. The reactor tubes were charged with a phosphorus-vanadium catalyst. The reactor was operated under the following conditions: the space velocity of the reactor was maintained between about 1000 hour$^{-1}$ to about 3000 hours$^{-1}$; the concentration of n-butane in the reactor feed stream was maintained between 1.5 mole percent to about 5.0 mole percent; the reactor temperature was maintained between about 325° C. to about 500° C.; and the reactor pressure was maintained between about 18 psig to about 28 psig. To control reactor temperature, liquid trimethyl phosphate was injected into a three inch n-butane feed line prior to mixing the n-butane with air to form a reactor feed stream. The concentration of trimethyl phosphate in the reactor feed stream was maintained at between about 1 ppmw to about 20 ppmw. The total residence time of trimethyl phosphate in the n-butane feed line and reactor feed stream prior to introduction into the reactor was less than one second.

After 24 months of operation, the reactor was shut down. Visual inspection of the reactor revealed very heavy deposits of trimethyl phosphate or trimethyl phosphate decomposition products on the reactor inlet head and piping. The reactor was then operated for an additional nine months under substantially the same conditions as described above. At the end of the nine month period, the reactor was shut down, cleaned and repacked with phosphorus-vanadium catalyst.

The repacked reactor was then operated for an additional 18 months under substantially the same conditions as described above. At the end of the 18 month period, the reactor was shut down. Visual inspection of the reactor revealed moderately heavy deposits of trimethyl phosphate or trimethyl phosphate decomposition products on the reactor inlet head, piping and rupture disc housings. The reactor was brought back into operation.

Approximately two months later, the method used to introduce the trimethyl phosphate to the reactor was modified. The injection port for the addition of trimethyl phosphate into the n-butane feed line was moved further upstream so that a first amount of trimethyl phosphate passed through an in-line butane filter. This arrangement increased the surface area for impingement of non-vaporized trimethyl phosphate droplets and thereby operated as a trimethyl phosphate vaporization means. The trimethyl phosphate was introduced through a sintered metal tip welded to ½ inch tubing, and inserted into the six inch butane feed line through a one inch ball valve and a packing gland designed for removal and insertion without shutting down the butane flow. A second (and smaller) amount of trimethyl phosphate was introduced downstream of the butane filter to further adjust the trimethyl phosphate concentration of the reactor feed stream introduced into the reactor. Placing the trimethyl phosphate injection port further upstream and passing the primary amount of trimethyl phosphate through the butane filter increased the residence time of the primary amount of trimethyl phosphate in the feed lines prior to introduction into the reactor to between about eight seconds to about 13 seconds.

The reactor was operated under substantially the same conditions as described above for an additional six months after installation of the modified trimethyl phosphate injection system. At the end of that six month period, the reactor was shut down. Visual inspection of the reactor revealed the reactor inlet head, piping and rupture disc housings to be substantially dry and free of deposits of trimethyl phosphate or trimethyl phosphate by-products. In fact, there appeared to be a reduction in deposits relative to the prior inspection.

EXAMPLE 2

REDUCTION IN TRIMETHYL PHOSPHATE DEPOSITS

A second multi-tubular fixed-bed catalytic reactor similar to the reactor in Example 1 was cleaned and the reactor tubes were repacked with phosphorus-vanadium catalyst. Before the reactor was brought back into operation, the trimethyl phosphate injection system was modified in the same manner as provided in Example 1. The reactor then was operated for 18 months under conditions substantially similar to those conditions described in Example 1. At the end of that 18 month period, the reactor was shut down. Visual inspection of the reactor revealed the reactor inlet head, piping and rupture disc housings to be substantially dry and free of deposits of trimethyl phosphate or trimethyl phosphate by-products.

EXAMPLE 3

REDUCTION IN VARIABILITY OF TRIMETHYL PHOSPHATE CONCENTRATION IN FEED STREAM

For the system comprising the reactor of Example 1, the concentration of trimethyl phosphate in the reactor feed stream introduced into the reactor was determined by on-line monitoring of the mass flows of the reactor feed stream and trimethyl phosphate feed stream followed by mass balance computation using the measured flow values. The concentration of trimethyl phosphate in the reactor feed stream was maintained within the range from about 1 ppmw to about 20 ppmw. Prior to installation of the modified trimethyl phosphate injection system as described in Example 1, a nitrogen pressurized trimethyl phosphate feed tank was used to control the flow of trimethyl phosphate from the feed tank into the n-butane feed line. After installation of the modified trimethyl phosphate injection system, a metering pump was used to control the flow of trimethyl phosphate from the feed tank to the injection port instead of using nitrogen pressure as the motive force for controlling the flow.

In general, for the period during which measurements were taken, the standard deviation of the trimethyl phosphate concentration in the reactor feed stream decreased from 1.1 to 0.3 ppm after conversion to the metering pump. With the nitrogen pressurized feed tank, the level of liquid trimethyl phosphate in the feed tank affected the trimethyl phosphate flow from the tank. Conversion to the metering pump largely eliminated this source of variability.

FIG. 1 illustrates the standard deviation of trimethyl phosphate concentration in the reactor feed stream where the addition was carried out using (1) a nitrogen pressurized trimethyl phosphate feed tank, and (2) a metering pump. The saw-tooth line in the top half of FIG. 1 shows the level of trimethyl phosphate in the trimethyl phosphate feed tank over time. The line in the bottom half of FIG. 1 shows the corresponding variability of trimethyl phosphate concentration in the reactor feed stream. The lefthand portion of this line corresponds to the variability of the trimethyl phosphate concentration in the reactor feed stream where the addition was carried out using the nitrogen pressurized trimethyl phosphate feed tank. The righthand portion of the line corresponds to the variability of the trimethyl phosphate concentration in the reactor feed stream where the addition was carried out using the metering pump. As shown in FIG. 1, the variability in trimethyl phosphate concentration was reduced by about 70% after conversion to the metering pump. While the overall average of trimethyl phosphate concentration in the feed stream was substantially the same for both methods of addition, use of the metering pump to reduce variability of concentration improved the ability to analyze and control other operating parameters.

Thus, it is apparent that there has been provided, in accordance with the instant invention, a process that fully satisfies the objects and advantages set forth above. While the invention has been described with respect to various embodiments thereof, it is understood that the invention is not limited thereto and that many alternatives, modifications, and variations will be apparent to those skilled in the art in light of the foregoing description. All references noted in this application are incorporated herein by reference.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. In a process for the preparation of maleic anhydride by reacting a hydrocarbon having at least four carbon atoms in a straight chain with molecular oxygen in a catalytic reactor, the reactor comprising a fixed catalyst bed having active sites comprising a vanadium-phosphorus-oxygen catalyst for the catalytic oxidation of the hydrocarbon to maleic anhydride, said process further comprising the continuous or intermittent introduction of a phosphorus-containing agent to the reactor, an improvement in the manner in which the phosphorus-containing agent is introduced into the reactor so as to improve the distribution of the phosphorus-containing agent throughout the reactor, the improved process comprising:

introducing the phosphorus-containing agent into a gaseous feed stream comprising the hydrocarbon, thereby providing a phosphorus-bearing hydrocarbon feed stream, combining the phosphorus-bearing hydrocarbon feed stream with molecular oxygen or a molecular oxygen-containing gas to form a reactor feed stream, and reacting the hydrocarbon with molecular oxygen in the reactor to produce a reaction product comprising maleic anhydride, the introduction of the phosphorus-containing agent into the hydrocarbon feed stream being controlled such that the phosphorus-containing agent is substantially vaporized before the reactor feed stream enters the catalyst bed.

2. In a process for the preparation of maleic anhydride by reacting a hydrocarbon having at least four carbon atoms in a straight chain with molecular oxygen in a catalytic reactor, the reactor comprising a fixed catalyst bed having active sites comprising a vanadium-phosphorus-oxygen catalyst for the catalytic oxidation of the hydrocarbon to maleic anhydride, said process further comprising the continuous or intermittent introduction of a liquid phosphorus-containing agent to the reactor, an improvement in the manner in which the phosphorus-containing agent is introduced into the reactor so as to improve the distribution of the phosphorus-containing agent throughout the reactor, the improved process comprising:

introducing the phosphorus-containing agent into a gaseous feed stream comprising the hydrocarbon, thereby providing a phosphorus-bearing hydrocarbon feed stream, combining the phosphorus-bearing hydrocarbon feed stream with molecular oxygen or a molecular oxygen-containing gas to form a reactor feed stream, and reacting the hydrocarbon with molecular oxygen in the reactor to produce a reaction product comprising maleic anhydride, the introduction of the phosphorus-containing agent into the hydrocarbon feed stream being controlled such that the phosphorus-containing agent is substantially uniformly distributed throughout the reactor feed stream before the reactor feed stream enters the catalyst bed.

3. In a process for the preparation of maleic anhydride by reacting a hydrocarbon having at least four carbon atoms in a straight chain with molecular oxygen in a catalytic reactor, the reactor comprising a fixed catalyst bed having active sites comprising a vanadium-phosphorus-oxygen catalyst for the catalytic oxidation of the hydrocarbon to maleic anhydride, the process further comprising the continuous or intermittent introduction of a phosphorus-containing agent to the reactor, an improvement in the manner in which the phosphorus-containing agent is introduced into the reactor so as to improve the distribution of the phosphorus-containing agent throughout the reactor, the improved process comprising:

introducing the phosphorus-containing agent into a feed stream comprising the hydrocarbon, thereby providing a phosphorus-bearing hydrocarbon feed stream, combining the hydrocarbon feed stream with molecular oxygen or a molecular oxygen-containing gas to form a reactor feed stream, and reacting the hydrocarbon with molecular oxygen in the reactor to produce a reaction product comprising maleic anhydride, the introduction of the phosphorus-containing agent into the hydrocarbon feed stream being controlled such that the residence time of the phosphorus-containing agent in the phosphorus-bearing hydrocarbon feed stream prior to the combination of the phosphorus-bearing hydrocarbon feed stream with molecular oxygen or molecular oxygen-containing gas is greater than one second.

4. The process of claim 3 wherein the residence time of the phosphorus-containing agent in the phosphorus-bearing hydrocarbon feed stream prior to the combination of the phosphorus-bearing hydrocarbon feed stream with the molecular oxygen or molecular oxygen-containing gas is greater than about three seconds.

5. The process of claim 3 wherein the residence time of the phosphorus-containing agent in the phosphorus-bearing hydrocarbon feed stream prior to the combination of the phosphorus-bearing hydrocarbon feed stream with the molecular oxygen or molecular oxygen-containing gas is greater than about five seconds.

6. The process of claim 3 wherein the residence time of the phosphorus-containing agent in the phosphorus-bearing hydrocarbon feed stream prior to the combination of the phosphorus-bearing hydrocarbon feed stream with the molecular oxygen or molecular oxygen-containing gas is greater than about eight seconds.

7. The process of claim 3 wherein the residence time of the phosphorus-containing agent in the phosphorus-bearing hydrocarbon feed stream prior to the combination of the phosphorus-bearing hydrocarbon feed stream with the molecular oxygen or molecular oxygen-containing gas is between about 2 seconds to about 90 seconds.

8. The process of claim 3 wherein the residence time of the phosphorus-containing agent in the phosphorus-bearing hydrocarbon feed stream prior to the combination of the phosphorus-bearing hydrocarbon feed stream with the molecular oxygen or molecular oxygen-containing gas is between about 8 seconds to about 15 seconds.

9. In a process for the preparation of maleic anhydride by reacting a hydrocarbon having at least four carbon atoms in a straight chain with molecular oxygen in a catalytic reactor, the reactor comprising a fixed catalyst bed having active sites comprising a vanadium-phosphorus-oxygen catalyst for the catalytic oxidation of the hydrocarbon to maleic anhydride, the process further comprising the continuous or intermittent introduction of a liquid phosphorus-containing agent to the reactor, an improvement in the manner in which the phosphorus-containing agent is introduced into the reactor so as to improve the distribution of the phosphorus-containing agent throughout the reactor, the improved process comprising:

introducing the phosphorus-containing agent into a gaseous feed stream comprising the hydrocarbon in a first mixing zone upstream of a gas/liquid contact zone, thereby producing a phosphorus-bearing hydrocarbon feed stream, the gas/liquid contact zone comprising a means for promoting interfacial contact between the liquid phosphorus-containing agent and the hydrocarbon feed gas;

combining the phosphorus-bearing hydrocarbon feed stream with molecular oxygen or a molecular oxygen-containing gas downstream of the gas/liquid contact zone to form a reactor feed stream, and reacting the hydrocarbon with molecular oxygen in the reactor to produce a reaction product comprising maleic anhydride.

10. The process of claim 9 wherein the hydrocarbon feed stream comprises droplets of liquid phosphorus-containing agent and the means serves to promote the reduction of the size of the droplets by providing a surface area for impingement of the droplets.

11. The process of claim 9 wherein the means comprises a means selected from the group consisting of filter media, static mixers, pipe fittings, and turbulence-inducing flow devices.

12. The process of claim 9 wherein the means comprises a filter medium.

13. The process of claim 9 wherein the means comprises a filter medium and serves to promote the reduction of the particle size of the phosphorus-containing agent and to promote the uniform distribution of the phosphorus-containing agent in the phosphorus-bearing hydrocarbon feed stream.

14. In a process for the preparation of maleic anhydride by reacting a hydrocarbon having at least four carbon atoms in a straight chain with molecular oxygen in a catalytic reactor, the reactor comprising a fixed catalyst bed having active sites comprising a vanadium-phosphorus-oxygen catalyst for the catalytic oxidation of the hydrocarbon to maleic anhydride, the process further comprising the continuous or intermittent introduction of a liquid phosphorus-containing agent to the reactor, an improvement in the manner in which the phosphorus-containing agent is introduced into the reactor so as to improve the distribution of the phosphorus-containing agent throughout the reactor, the improved process comprising:

introducing the liquid phosphorus-containing agent into a gaseous feed stream comprising the hydrocarbon in a first mixing zone upstream of a filter medium through which the hydrocarbon feed stream is passed, thereby providing a phosphorus-bearing hydrocarbon feed stream, combining the phosphorus-bearing hydrocarbon feed stream with molecular oxygen or a molecular oxygen-containing gas in an oxygen mixing zone downstream of the filter medium, and reacting the hydrocarbon with molecular oxygen in the reactor to produce a reaction product comprising maleic anhydride, the residence time of the phosphorus-bearing hydrocarbon feed stream between the first mixing zone and the oxygen mixing zone being greater than one second.

15. The process of claim 14 wherein the residence time of the phosphorus-bearing hydrocarbon feed stream between the first mixing zone and the oxygen mixing zone is greater than about three seconds.

16. The process of claim 14 wherein the residence time of the phosphorus-bearing hydrocarbon feed stream between the first mixing zone and the oxygen mixing zone is greater than about five seconds.

17. The process of claim 14 wherein the residence time of the phosphorus-bearing hydrocarbon feed stream between the first mixing zone and the oxygen mixing zone is greater than about eight seconds.

18. The process of claim 14 wherein the residence time of the phosphorus-bearing hydrocarbon feed stream between the first mixing zone and the oxygen mixing zone is between about 2 seconds to about 90 seconds.

19. The process of claim 14 wherein the residence time of the phosphorus-bearing hydrocarbon feed stream between the first mixing zone and the oxygen mixing zone is between about 8 seconds to about 15 seconds.

20. The process of claim 14 wherein the filter medium serves to promote the reduction of the particle size of the liquid phosphorus-containing agent and to promote the uniform distribution of the phosphorus-containing agent in the phosphorus-bearing hydrocarbon feed stream.

21. The process of claim 14 wherein the average particle size of the phosphorus-containing agent in the reactor feed stream is less than about $10\mu$.

22. The process of claim 14 wherein the average particle size of the phosphorus-containing agent in the reactor feed stream is less than about $5\mu$.

23. The process of claim 14 wherein average particle size of the phosphorus-containing agent in the reactor feed stream is less than about $3\mu$.

24. The process of claim 14 wherein the phosphorus-containing agent is preheated to a temperature greater than about 20° C. below the temperature of the hydrocarbon feed stream before the agent is introduced into the hydrocarbon feed stream.

25. The process of claim 14 wherein the phosphorus-containing agent is preheated to a temperature greater than about 10° C. below the temperature of the hydrocarbon feed stream before the agent is introduced into the hydrocarbon feed stream.

26. The process of claim 14 wherein the phosphorus-containing agent is preheated to a temperature of at least 70° C. before the agent is introduced into the hydrocarbon feed stream.

27. The process of claim 14 wherein the phosphorus-containing agent is injected into the hydrocarbon feed stream.

28. The process of claim 14 wherein the phosphorus-containing agent is introduced into the hydrocarbon feed stream through a tube inserted into the hydrocarbon feed stream, wherein the tube comprises a fritted tip through which the phosphorus-containing agent exits the tube.

29. The process of claim 14 wherein the phosphorus-containing agent is introduced into the hydrocarbon feed stream through a tube inserted into the hydrocarbon feed stream substantially perpendicular to the direction of the flow of the hydrocarbon feed stream, wherein the tube comprises a fritted tip through which the phosphorus-containing agent exits the tube.

30. The process of claim 14 wherein the phosphorus-bearing hydrocarbon feed strewn is divided into two or more separate feed streams for use in two or more separate catalytic reactors.

31. The process of claim 14 wherein the process further comprises introducing the phosphorus-containing agent at a first rate into the hydrocarbon feed stream thereby forming a phosphorus-bearing hydrocarbon feed stream, and introducing additional phosphorus-containing agent at a second rate into the phosphorus-bearing hydrocarbon feed steam downstream from where the phosphorus-containing agent is introduced into the hydrocarbon feed stream.

32. The process of claim 14 wherein the ratio of the first rate to the second rate is at least about 3:1.

33. The process of claim 14 wherein the ratio of the first rate to the second rate is at least about 4:1.

34. The process of claim 14 wherein the process further comprises introducing additional phosphorus-containing agent into the phosphorus-bearing hydrocarbon feed stream downstream from the filter medium.

35. The process of claim 14 wherein the phosphorus-containing agent comprises an alkyl ester of orthophosphoric acid or an alkyl ester of an orthophosphoric acid derivative.

36. The process of claim 14 wherein the phosphorus-containing agent comprises an alkyl ester of orthophosphoric acid having the following structure:

$$(RO)_3P{=}O \qquad (I)$$

or an alkyl ester of an orthophosphoric acid derivative having the following structure:

$$(RO)_3P \qquad (II)$$

wherein R is hydrogen or a $C_1$ to $C_4$ alkyl, at least one R being a $C_1$ to $C_4$ alkyl.

37. The process of claim 14 wherein the phosphorus-containing agent is selected from the group consisting of trialkyl phosphates and trialkyl phosphites.

38. The process of claim 14 wherein the phosphorus-containing agent is selected from the group consisting of trimethyl phosphate, triethyl phosphate, trimethyl phosphite and triethyl phosphite.

39. The process of claim 14 wherein the phosphorus-containing agent is trimethyl phosphate.

40. The process of claim 14 wherein the concentration of the phosphorus-containing agent in the reactor feed stream is about 1 ppmw to about 20 ppmw.

41. The process of claim 14 wherein the concentration of the phosphorus-containing agent in the reactor feed stream is about 4 ppmw to about 17 ppmw.

42. The process of claim 14 wherein the concentration of the phosphorus-containing agent in the reactor feed stream is about 7 ppmw to about 14 ppmw.

43. The process of claim 14 wherein the rate at which the phosphorus-containing agent is introduced into the catalytic reactor is between about 0.005 g per kilogram of total bed catalyst per day to about 5 g per kilogram of the total catalyst in the bed per day.

44. The process of claim 14 wherein the catalyst has a phosphorus/vanadium atom ratio of from about 0.95 to about 1.2.

45. The process of claim 14 wherein the hydrocarbon is a saturated hydrocarbon.

46. The process of claim 14 wherein the hydrocarbon is n-butane.

47. The process of claim 14 wherein the molecular oxygen-containing gas is air.

48. The process of claim 14 wherein the hydrocarbon-in-air concentration is from about 1 mole percent to about 10 mole percent.

49. The process of claim 14 wherein the hydrocarbon-in-air concentration is from about 1.5 mole percent to about 4 mole percent.

50. The process of claim 14 wherein the reaction is conducted at a temperature of from about 300° C. to about 600° C., the pressure is from about 14.7 psig to about 50.0 psig, and the space velocity is about 100 $hour^{-1}$ to about 4000 $hour^{-1}$.

51. The process of claim 14 wherein the reaction is conducted at a temperature of from about 325° C. to about 500° C., the pressure is from about 18.0 psig to about 30.0 psig, and the space velocity is about 1000 $hour^{-1}$ to about 3000 $hours^{-1}$.

52. The process of claim 14 wherein the reaction is conducted at a temperature of from about 425° C. to about 450° C., the pressure is from about 20.0 psig to about 28.0 psig, and the space velocity is about 1700 $hours^{-1}$ to about 2500 $hour^{-1}$.

53. The process of claim 14 wherein the conversion of the hydrocarbon introduced to the reactor is at least about 70%.

54. The process of claim 14 wherein the maleic anhydride yield is at least 45 mole percent.

55. The process of claim 14 wherein the average yield decay is less than about 0.25% per month.

56. In a process for the preparation of maleic anhydride by reacting a hydrocarbon having at least four carbon atoms in a straight chain with molecular oxygen in a catalytic reactor, the reactor comprising a fixed catalyst bed having active sites comprising a vanadium-phosphorus-oxygen catalyst for the catalytic oxidation of the hydrocarbon to maleic anhydride, the process further comprising the continuous or intermittent introduction of a liquid phosphorus-containing agent to the reactor, an improvement in the manner in which the phosphorus-containing agent is introduced into the reactor so as to improve the distribution of the phosphorus-containing agent throughout the reactor, the improved process comprising:

introducing the phosphorus-containing agent into a gaseous feed stream comprising the hydrocarbon in a first mixing zone, thereby providing a phosphorus-bearing hydrocarbon feed stream, passing the phosphorus-bearing feed stream through a filter medium that intercepts the liquid phosphorus-containing agent and distributes it within the medium laterally across the flow path of the hydrocarbon feed stream, thereby dispersing the phosphorus-containing agent to promote uniform radial distribution of the liquid phosphorus-containing agent within the phosphorus-bearing hydrocarbon stream as the liquid is re-entrained therein from the filter medium, combining the phosphorus-bearing hydrocarbon feed stream with molecular oxygen or a molecular oxygen-containing gas in an oxygen mixing zone downstream of said filter medium, and reacting the hydrocarbon with molecular oxygen in the reactor to produce a reaction product comprising maleic anhydride.

57. A process as set forth in claim 56 wherein the liquid phosphorus-containing agent is re-entrained in droplets presenting a high surface area effective to promote vaporization of the phosphorus-containing agent in the gas stream upon mixing with the oxygen-containing gas.

58. A process as set forth in claim 57 wherein the particle size of said droplets is between about 1 and about 5µ.

59. A process as set forth in claim 58 wherein the filter medium comprises a porous medium having an average pore size of between about 1 and about 5µ.

60. A process as set forth in claim 56 wherein said filter medium extends substantially across the entire flow path of the phosphorus-bearing hydrocarbon feed stream.

61. In a process for the preparation of maleic anhydride by reacting a hydrocarbon having at least four carbon atoms in a straight chain with molecular oxygen in a catalytic reactor, the reactor comprising a fixed catalyst bed having active sites comprising a vanadium-phosphorus-oxygen catalyst for the catalytic oxidation of the hydrocarbon to maleic anhydride, the process further comprising the continuous or intermittent introduction of a phosphorus-containing agent to the reactor, an improvement in the manner in which the phosphorus-containing agent is introduced into the reactor so as to improve the distribution of the phosphorus-containing agent throughout the reactor, the improved process comprising:

introducing the phosphorus-containing agent into a gaseous feed stream comprising the hydrocarbon in a first mixing zone, thereby providing a phosphorus-bearing hydrocarbon feed stream, passing the phosphorus-bearing feed stream through a conduit comprising a flow restriction comprising means for dispersing the phosphorus-containing agent to promote uniform radial distribution of the phosphorus-containing agent within the phosphorus-bearing hydrocarbon stream, combining the phosphorus-bearing hydrocarbon feed stream with molecular oxygen or a molecular oxygen-containing gas in an oxygen mixing zone downstream of said flow restriction comprising means, and reacting the hydrocarbon with molecular oxygen in the reactor to produce a reaction product comprising maleic anhydride.

62. A process as set forth in claim 61 wherein said phosphorus-containing agent comprises a liquid, and said flow restriction comprises a gas/liquid contact zone comprising means effective to promote interfacial contact between the liquid phosphorus-containing agent and the hydrocarbon gas.

63. A process as set forth in claim 62 wherein passage of the phosphorus-bearing hydrocarbon feed stream through said gas/liquid contact zone is effective to reduce the average particle size of liquid droplets of phosphorus-containing agent dispersed in a gasesous hydrocarbon.

64. A process as set forth in claim 63 wherein the average particle size of the liquid droplets is reduced to a size effective to promote vaporization of said liquid phosphorus-containing agent after the phosphorus-bearing hydrocarbon stream is mixed with said oxygen-containing gas.

65. A process as set forth in claim 64 wherein said gas/liquid contact zone comprises impingement surfaces for said liquid droplets and/or means for promoting vaporization of the droplets.

66. A process as set forth in claim 61 wherein said flow restriction is selected from the group consisting of filter media, static mixers, pipe fittings, and turbulence inducing flow devices.

67. In a process for the preparation of maleic anhydride by reacting a hydrocarbon having at least four carbon atoms in a straight chain with molecular oxygen in a catalytic reactor, the reactor comprising a fixed catalyst bed having active sites comprising a vanadium-phosphorus-oxygen catalyst for the catalytic oxidation of the hydrocarbon to maleic anhydride, the process further comprising the continuous or intermittent introduction of a phosphorus-containing agent to the reactor, an improvement in the manner in which the phosphorus-containing agent is introduced into the reactor so as to improve the distribution of the phosphorus-containing agent throughout the reactor, the improved process comprising:

introducing the phosphorus-containing agent into a feed stream comprising the hydrocarbon in a first mixing zone at a first rate, thereby providing a first phosphorus-bearing hydrocarbon feed stream, passing the first phosphorus-bearing hydrocarbon feed stream through a first conduit to a second mixing zone, introducing additional phosphorus-containing agent into the first phosphorus-bearing hydrocarbon feed stream in a second mixing zone at a second rate, thereby providing a second phosphorus-bearing hydrocarbon feed stream, passing the second phosphorus-bearing hydrocarbon feed stream through a second conduit to an oxygen mixing zone and mixing the phosphorus-bearing hydrocarbon feed stream with molecular oxygen or a molecular oxygen-containing gas in the oxygen mixing zone to form a reactor feed stream, the sum of the residence time of the first phosphorus-bearing hydrocarbon feed stream between the first mixing zone and the second mixing zone and the residence time of the second phosphorus-bearing hydrocarbon feed stream between the second mixing zone and the oxygen mixing zone being greater than one second, and reacting the hydrocarbon with molecular oxygen in the reactor to produce a reaction product comprising maleic anhydride.

68. The process of claim 67 wherein the ratio of the first rate to the second rate is at least about 3:1.

69. The process of claim 67 wherein the ratio of the first rate to the second rate is at least about 4:1.

70. In the operation of a catalytic reactor for preparing maleic anhydride by reacting a hydrocarbon having at least four carbon atoms in a straight chain with molecular oxygen, each reactor comprising a fixed catalyst bed having active sites comprising a vanadium-phosphorus-oxygen catalyst for the catalytic oxidation of the hydrocarbon to maleic anhydride, an improvement in controlling the introduction of a phosphorus-containing agent into the reactor, the improved process comprising:

dividing a supply of phosphorus-containing agent between a primary supply for delivery to a primary mixing zone and a secondary supply for delivery to a secondary mixing zone downstream of said primary mixing zone with respect to the flow of hydrocarbon gas to said reactor;

measuring the rate of flow of hydrocarbon gas entering said primary mixing zone;

controlling the rate at which said primary supply of phosphorus-containing agent is introduced into said primary mixing zone to provide a predetermined minimum concentration of said phosphorus-containing agent in a primary phosphorus-bearing hydrocarbon stream exiting said primary mixing zone; and introducing said secondary supply of phosphorus-containing agent and said primary phosphorus-bearing hydrocarbon stream into said secondary mixing zone to produce an adjusted phosphorus-bearing hydrocarbon stream; and mixing said adjusted phosphorus-bearing hydrocarbon feed stream with an oxygen-containing gas to provide said reactor feed stream;

the rate at which said secondary supply of said phosphorus-containing agent is introduced into said secondary mixing zone being controlled to provide a total concentration of phosphorus-containing agent in said adjusted phosphorus-bearing hydrocarbon stream corresponding to a predetermined concentration having a hydrocarbon to phosphorus-containing compound ratio effective to provide a target concentration of phosphorus in said reactor feed gas entering said catalyst bed.

71. A process as set forth in claim 70 wherein the phosphorus-bearing hydrocarbon stream exiting said primary mixing zone and said secondary supply of said phosphorus-containing agent are each divided into a plurality of secondary streams for separate supply to a plurality of secondary mixing zones downstream of said primary mixing zone, and the adjusted phosphorus-bearing hydrocarbon feed stream exiting each of said secondary mixing zones is delivered to a corresponding reactor of a plurality of reactors each supplied from a separate secondary mixing zone.

72. A process as set forth in claim 71 wherein the concentration of phosphorus-containing agent in the phosphorus-bearing hydrocarbon stream exiting said primary mixing zone is equal to or lower than a predetermined concentration having a hydrocarbon to phosphorus-containing compound ratio effective to provide the lowest of the target concentrations of phosphorus in the reactor feed gases respectively entering the catalyst beds of said plurality of reactors.

73. A process as set forth in claim 72 wherein the rate of introduction of phosphorus-containing compound into each of the plurality of secondary mixing zones is controlled to provide a predetermined concentration having a hydrocarbon to phosphorus-containing compound ratio effective to provide a target concentration of phosphorus in the reactor feed gas entering the catalyst bed to which the stream exiting such secondary mixing zone is directed.

74. In the operation of a catalytic reactor for preparing maleic anhydride by reacting a hydrocarbon having at least four carbon atoms in a straight chain with molecular oxygen, each reactor comprising a fixed catalyst bed having active sites comprising a vanadium-phosphorus-oxygen catalyst for the catalytic oxidation of the hydrocarbon to maleic anhydride, an improvement in controlling the introduction of a phosphorus-containing agent into the reactor, the improved process comprising:

dividing a supply of phosphorus-containing agent between a primary supply for delivery to said primary mixing zone and a secondary supply for delivery to a secondary mixing zone downstream of said primary mixing zone with respect to the flow of hydrocarbon gas to said reactor;

measuring the rate of flow of hydrocarbon gas entering said primary mixing zone;

controlling the rate at which the primary supply of said phosphorus-containing agent is introduced into said primary mixing zone to provide a predetermined minimum concentration of said phosphorus-containing agent in a primary phosphorus-bearing hydrocarbon stream exiting said primary mixing zone; and introducing said secondary supply of said phosphorus-containing agent and another stream comprising said primary phosphorus bearing hydrocarbon stream into said secondary mixing zone to produce an adjusted phosphorus-bearing stream;

the rate of introduction of said secondary supply of said phosphorus-containing agent into said secondary mixing zone being controlled to provide a total concentration of phosphorus-containing agent in said adjusted phosphorus-bearing hydrocarbon stream corresponding to a predetermined concentration having a hydrocarbon to phosphorus-containing compound ratio effective to provide a target concentration of phosphorus in said reactor feed gas entering said catalyst bed.

75. A process as set forth in claim 74 wherein said primary phosphorus-bearing hydrocarbon stream is mixed with phosphorus-containing agent introduced into said secondary mixing zone.

76. A process as set forth in claim 74 wherein said primary phosphorus-bearing hydrocarbon stream is mixed with an oxygen containing gas to produce a pre-adjusted reactor feed gas; and said pre-adjusted reactor feed gas is mixed with phosphorus-containing agent introduced into said secondary mixing zone to produce an adjusted reactor feed stream.

77. In the operation of a plurality of catalytic reactors for preparing maleic anhydride by reacting a hydrocarbon having at least four carbon atoms in a straight chain with molecular oxygen, each reactor comprising a fixed catalyst bed having active sites comprising a vanadium-phosphorus-oxygen catalyst for the catalytic oxidation of the hydrocarbon to maleic anhydride, an improvement in controlling the continuous or intermittent introduction of a phosphorus-containing agent into the reactor, the improved process comprising:

measuring the flow rate of a feed stream comprising the hydrocarbon, calculating a first rate of addition of the phosphorus-containing agent to be introduced into the hydrocarbon feed stream, controlling the introduction of the phosphorus-containing agent into the hydrocarbon feed stream in accordance with the calculated first rate of addition, the phosphorus-containing agent being introduced into the hydrocarbon feed stream in a first mixing zone, thereby providing a primary phosphorus-bearing hydrocarbon feed stream, the primary phosphorus-bearing hydrocarbon feed stream passing through a first conduit to a manifold where the primary phosphorus-bearing hydrocarbon feed stream is divided into a plurality of secondary hydrocarbon feed streams passing through a series of second conduits to a series of second mixing zones, calculating a second rate of addition of the phosphorus-containing agent to be optionally introduced into each secondary hydrocarbon feed stream, controlling the introduction of the phosphorus-containing agent into each secondary hydrocarbon feed stream in accordance with each corresponding calculated second rate of addition, the phosphorus-containing agent being optionally introduced into each secondary hydrocarbon feed stream in each second mixing zone, thereby providing a plurality of secondary phosphorus-bearing hydrocarbon feed streams, the second rate of addition of the phosphorus-containing agent introduced into each secondary hydrocarbon feed stream being independent of the second rate of addition of the phosphorus-containing agent introduced into each of the other secondary hydrocarbon feed streams, mixing each secondary phosphorus-bearing hydrocarbon feed stream with molecular oxygen or a molecular oxygen-containing gas in an oxygen mixing zone, thereby producing a plurality of secondary reactor feed streams that are introduced into separate catalytic reactors, the sum of the residence time of the primary phosphorus-bearing hydrocarbon feed stream between the first mixing zone and the manifold, the residence time of the secondary hydrocarbon feed stream between the manifold and the second mixing zone, and the residence time of the secondary phosphorus-bearing hydrocarbon feed stream between the second mixing zone and the oxygen mixing zone being greater than one second, and reacting the hydrocarbon with molecular oxygen in each catalytic reactor to produce a reaction product comprising maleic anhydride, wherein the first rate of addition corresponds to a minimum predetermined rate of addition of the phosphorus-containing agent as a function of the measured flow rate of the hydrocarbon feed stream, and wherein the second rate of addition is calculated independently for each secondary hydrocarbon feed stream as a function of the measured flow rate of the hydrocarbon feed stream and corresponds to a final target rate of addition of phosphorus-containing agent for the reactor into which the secondary reactor feed stream is to be introduced as reduced to account for the portion of the phosphorus-containing agent previously introduced in the first mixing zone that is contained in the secondary reactor feed stream.

78. In the operation of a catalytic reactor for preparing maleic anhydride by reacting a hydrocarbon having at least four carbon atoms in a straight chain with molecular oxygen, each reactor comprising a fixed catalyst bed having active sites comprising a vanadium-phosphorus-oxygen catalyst for the catalytic oxidation of the hydrocarbon to maleic anhydride, an improvement in the controlling the continuous or intermittent introduction of a phosphorus-containing agent into the reactor, the improved process comprising:

measuring the flow rate of a feed stream comprising the hydrocarbon, calculating a first rate of addition of phosphorus-containing agent to be introduced into the hydrocarbon feed stream, controlling the introducing of the phosphorus-containing agent into the hydrocarbon feed stream in accordance with the calculated first rate of addition, the phosphorus-containing agent being introduced into the hydrocarbon feed stream in a first mixing zone, thereby providing a first phosphorus-bearing hydrocarbon feed stream, the first phosphorus-bearing hydrocarbon feed stream passing through a first conduit to a second mixing zone, calculating a second rate of addition of phosphorus-containing agent to be optionally introduced into the first phosphorus-bearing hydrocarbon feed stream, controlling the introduction of the phosphorus-containing agent into the first phosphorus-bearing hydrocarbon feed stream in accordance with the calculated rate of addition, the phosphorus-containing agent being introduced into the first phosphorus-bearing hydrocarbon feed stream in the second mixing zone, thereby providing a second phosphorus-bearing hydrocarbon feed stream, combining the second phosphorus-bearing hydrocarbon feed stream with molecular oxygen or a molecular oxygen-containing gas in an oxygen mixing zone to form a reactor feed stream, the sum of the residence time of the first phosphorus-bearing hydrocarbon feed stream between the first mixing zone and the second mixing zone and the residence time of the second phosphorus-bearing hydrocarbon feed stream between the second mixing zone and the oxygen mixing zone being greater than one second, and reacting the hydrocarbon with molecular oxygen in the reactor to produce a reaction product comprising maleic anhydride, wherein the first rate of addition corresponds to a minimum predetermined rate of addition of the phosphorus-containing agent as a function of the measured flow rate of the hydrocarbon feed stream, and wherein the second rate of addition is calculated as a function of the measured flow rate of the hydrocarbon feed stream and corresponds to a final target rate of addition of phosphorus-containing agent for the reactor as reduced to account for the phosphorus-containing agent previously introduced in the first mixing zone.

79. The process of claim 78 wherein the introduction of the phosphorus-containing agent in the first mixing zone and the second mixing zone is controlled by one or more PID controllers.

* * * * *